US011911011B2

(12) United States Patent
Mintz et al.

(10) Patent No.: US 11,911,011 B2
(45) Date of Patent: *Feb. 27, 2024

(54) ENDOLUMENAL OBJECT SIZING

(71) Applicant: Auris Health, Inc., Redwood City, CA (US)

(72) Inventors: David S. Mintz, Mountain View, CA (US); David M. Schummers, Oakland, CA (US); Prasanth Jeevan, San Mateo, CA (US); Hedyeh Rafii-Tari, Mountain View, CA (US); Ritwik Ummalaneni, San Mateo, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/734,268

(22) Filed: May 2, 2022

(65) Prior Publication Data

US 2022/0330808 A1 Oct. 20, 2022

Related U.S. Application Data

(63) Continuation of application No. 16/179,568, filed on Nov. 2, 2018, now Pat. No. 11,337,602, which is a (Continued)

(51) Int. Cl.
*A61B 1/307* (2006.01)
*A61B 34/30* (2016.01)
(Continued)

(52) U.S. Cl.
CPC .......... *A61B 1/307* (2013.01); *A61B 1/00009* (2013.01); *A61B 1/000094* (2022.02);
(Continued)

(58) Field of Classification Search
CPC ................ A61B 1/307; A61B 1/00009; A61B 1/000094; A61B 1/04; A61B 1/06;
(Continued)

(56) References Cited

U.S. PATENT DOCUMENTS 6,459,481 B1  10/2002  Schaack
9,504,604 B2  11/2016  Alvarez
(Continued)

OTHER PUBLICATIONS

Final Rejection for U.S. Appl. No. 15/392,674, dated Sep. 22, 2017, 8 pages.
(Continued)

*Primary Examiner* — Peter Luong
(74) *Attorney, Agent, or Firm* — Chang & Hale LLP

(57) ABSTRACT

An object sizing system sizes an object positioned within a patient. The object sizing system identifies a presence of the object. The object sizing system navigates an elongate body of an instrument to a position proximal to the object within the patient. An imaging sensor coupled to the elongate body captures one or more sequential images of the object. The instrument may be further moved around within the patient to capture additional images at different positions/orientations relative to the object. The object sizing system also acquires robot data and/or EM data associated with the positions and orientations of the elongate body. The object sizing system analyzes the captured images based on the acquired robot data to estimate a size of the object.

20 Claims, 23 Drawing Sheets

Related U.S. Application Data continuation of application No. 15/392,674, filed on Dec. 28, 2016, now Pat. No. 10,136,959.

(51) Int. Cl.

| | | |
|---|---|---|
| *A61B 34/32* | (2016.01) | |
| *A61B 90/00* | (2016.01) | |
| *A61B 5/107* | (2006.01) | |
| *A61B 5/06* | (2006.01) | |
| *A61B 1/00* | (2006.01) | |
| *A61B 1/04* | (2006.01) | |
| *A61B 1/06* | (2006.01) | |
| *A61B 34/20* | (2016.01) | |

(52) U.S. Cl.
CPC .................. *A61B 1/04* (2013.01); *A61B 1/06* (2013.01); *A61B 5/062* (2013.01); *A61B 5/107* (2013.01); *A61B 34/30* (2016.02); *A61B 34/32* (2016.02); *A61B 90/37* (2016.02); *A61B 2034/2051* (2016.02); *A61B 2034/303* (2016.02); *A61B 2090/061* (2016.02); *A61B 2090/364* (2016.02)

(58) Field of Classification Search
CPC ......... A61B 5/062; A61B 5/107; A61B 34/30; A61B 34/32; A61B 90/37; A61B 2034/2051; A61B 2034/303; A61B 2090/061; A61B 2090/364
See application file for complete search history.

(56) References Cited

U.S. PATENT DOCUMENTS

| | | | |
|---|---|---|---|
| 9,561,083 B2 | 2/2017 | Yu et al. |
| 9,622,827 B2 | 4/2017 | Yu et al. |
| 9,636,184 B2 | 5/2017 | Lee et al. |
| 9,713,509 B2 | 7/2017 | Schuh et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,080,576 B2 | 9/2018 | Romo et al. |
| 10,136,959 B2 | 11/2018 | Mintz et al. |
| 10,145,747 B1 | 12/2018 | Lin et al. |
| 10,149,720 B2 | 12/2018 | Romo |
| 10,159,532 B1 | 12/2018 | Ummalaneni |
| 10,159,533 B2 | 12/2018 | Moll et al. |
| 10,169,875 B2 | 1/2019 | Mintz et al. |
| 10,434,660 B2 | 10/2019 | Meyer et al. |
| 10,464,209 B2 | 11/2019 | Ho et al. |
| 10,470,830 B2 | 11/2019 | Hill et al. |
| 10,482,599 B2 | 11/2019 | Mintz et al. |
| 10,517,692 B2 | 12/2019 | Eyre et al. |
| 10,524,866 B2 | 1/2020 | Srinivasan et al. |
| 10,539,478 B2 | 1/2020 | Lin et al. |
| 10,555,778 B2 | 2/2020 | Ummalaneni |
| 10,639,114 B2 | 5/2020 | Schuh et al. |
| 10,667,875 B2 | 6/2020 | DeFonzo et al. |
| 10,702,348 B2 | 7/2020 | Moll et al. |
| 10,743,751 B2 | 8/2020 | Landey et al. |
| 10,751,140 B2 | 8/2020 | Wallace et al. |
| 10,765,303 B2 | 9/2020 | Graetzel et al. |
| 10,765,487 B2 | 9/2020 | Ho et al. |
| 2004/0258328 A1 | 12/2004 | Adler |
| 2005/0228252 A1 | 10/2005 | Neason |
| 2007/0084027 A1* | 4/2007 | Walczak ............... A61G 17/08 27/1 |
| 2007/0197896 A1 | 8/2007 | Moll et al. |
| 2008/0225505 A1 | 9/2008 | Martin et al. |
| 2008/0255505 A1* | 10/2008 | Carlson ............. A61M 25/0662 604/95.04 |
| 2014/0142591 A1 | 5/2014 | Alvarez et al. |
| 2014/0309649 A1 | 10/2014 | Alvarez et al. |
| 2014/0336461 A1 | 11/2014 | Reiter et al. |
| 2014/0357984 A1 | 12/2014 | Wallace et al. |
| 2014/0364870 A1 | 12/2014 | Alvarez et al. |
| 2014/0379000 A1 | 12/2014 | Romo et al. |
| 2015/0051592 A1 | 2/2015 | Kintz |
| 2015/0101442 A1 | 4/2015 | Romo |
| 2015/0119638 A1 | 4/2015 | Yu et al. |
| 2015/0164594 A1 | 6/2015 | Romo et al. |
| 2015/0164596 A1 | 6/2015 | Romo et al. |
| 2015/0335480 A1 | 11/2015 | Alvarez et al. |
| 2016/0001038 A1 | 1/2016 | Romo et al. |
| 2016/0270865 A1 | 9/2016 | Landey et al. |
| 2016/0287279 A1 | 10/2016 | Bovay et al. |
| 2016/0296294 A1 | 10/2016 | Moll et al. |
| 2016/0374541 A1 | 12/2016 | Agrawal et al. |
| 2017/0007337 A1 | 1/2017 | Dan |
| 2017/0065364 A1 | 3/2017 | Schuh et al. |
| 2017/0065365 A1 | 3/2017 | Schuh |
| 2017/0100199 A1 | 4/2017 | Yu et al. |
| 2017/0119413 A1 | 5/2017 | Romo |
| 2017/0119481 A1 | 5/2017 | Romo et al. |
| 2017/0165011 A1 | 6/2017 | Bovay et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0290631 A1 | 10/2017 | Lee et al. |
| 2017/0333679 A1 | 11/2017 | Jiang |
| 2017/0340396 A1 | 11/2017 | Romo et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0177383 A1 | 6/2018 | Noonan et al. |
| 2018/0177556 A1 | 6/2018 | Noonan |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0110839 A1 | 4/2019 | Rafii-Tari et al. |
| 2019/0151148 A1 | 5/2019 | Alvarez et al. |
| 2019/0167366 A1 | 6/2019 | Ummalaneni et al. |
| 2019/0175062 A1 | 6/2019 | Rafii-Tari et al. |
| 2019/0175799 A1 | 6/2019 | Hsu et al. |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre et al. |
| 2019/0223974 A1 | 7/2019 | Romo et al. |
| 2019/0228525 A1 | 7/2019 | Mintz et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |

(56) References Cited

U.S. PATENT DOCUMENTS

| | | |
|---|---|---|
| 2019/0298460 A1 | 10/2019 | Al-Jadda et al. |
| 2019/0298465 A1 | 10/2019 | Chin et al. |
| 2019/0336238 A1 | 11/2019 | Yu et al. |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0375383 A1 | 12/2019 | Auer |
| 2019/0380787 A1 | 12/2019 | Ye et al. |
| 2019/0380797 A1 | 12/2019 | Yu et al. |
| 2020/0000533 A1 | 1/2020 | Schuh et al. |
| 2020/0022767 A1 | 1/2020 | Hill et al. |
| 2020/0038123 A1 | 2/2020 | Graetzel et al. |
| 2020/0039086 A1 | 2/2020 | Meyer et al. |
| 2020/0046434 A1 | 2/2020 | Graetzel et al. |
| 2020/0054408 A1 | 2/2020 | Schuh et al. |
| 2020/0060516 A1 | 2/2020 | Baez, Jr. |
| 2020/0085516 A1 | 3/2020 | DeFonzo et al. |
| 2020/0093549 A1 | 3/2020 | Chin et al. |
| 2020/0093554 A1 | 3/2020 | Schuh et al. |
| 2020/0100845 A1 | 4/2020 | Julian |
| 2020/0100855 A1 | 4/2020 | Leparmentier et al. |
| 2020/0101264 A1 | 4/2020 | Jiang |
| 2020/0107894 A1 | 4/2020 | Wallace et al. |
| 2020/0121502 A1 | 4/2020 | Kintz |
| 2020/0146769 A1 | 5/2020 | Eyre et al. |
| 2020/0170720 A1 | 6/2020 | Ummalaneni |
| 2020/0171660 A1 | 6/2020 | Ho et al. |
| 2020/0188043 A1 | 6/2020 | Yu et al. |
| 2020/0197112 A1 | 6/2020 | Chin et al. |
| 2020/0206472 A1 | 7/2020 | Ma et al. |
| 2020/0217733 A1 | 7/2020 | Lin et al. |
| 2020/0222134 A1 | 7/2020 | Schuh et al. |
| 2020/0237458 A1 | 7/2020 | DeFonzo et al. |
| 2020/0261172 A1 | 8/2020 | Romo et al. |
| 2020/0268459 A1 | 8/2020 | Noonan |
| 2020/0268460 A1 | 8/2020 | Tse et al. |
| 2020/0281787 A1 | 9/2020 | Ruiz |

OTHER PUBLICATIONS

Non-Final Rejection for U.S. Appl. No. 15/392,674, dated Mar. 20, 2017, 7 pages.
Non-Final Rejection for U.S. Appl. No. 16/179,568, dated Mar. 25, 2021, 6 pages.
Notice Of Allowance for U.S. Appl. No. 16/179,568, dated Jan. 18, 2022, 8 pages.
Notice of Allowance for U.S. Appl. No. 15/392,674, dated Feb. 27, 2018, 8 pages.
Notice of Allowance for U.S. Appl. No. 15/392,674, dated Jul. 18, 2018, 5 pages.
Office action for U.S. Appl. No. 16/179,568, dated Sep. 22, 2021, 7 pages.

\* cited by examiner

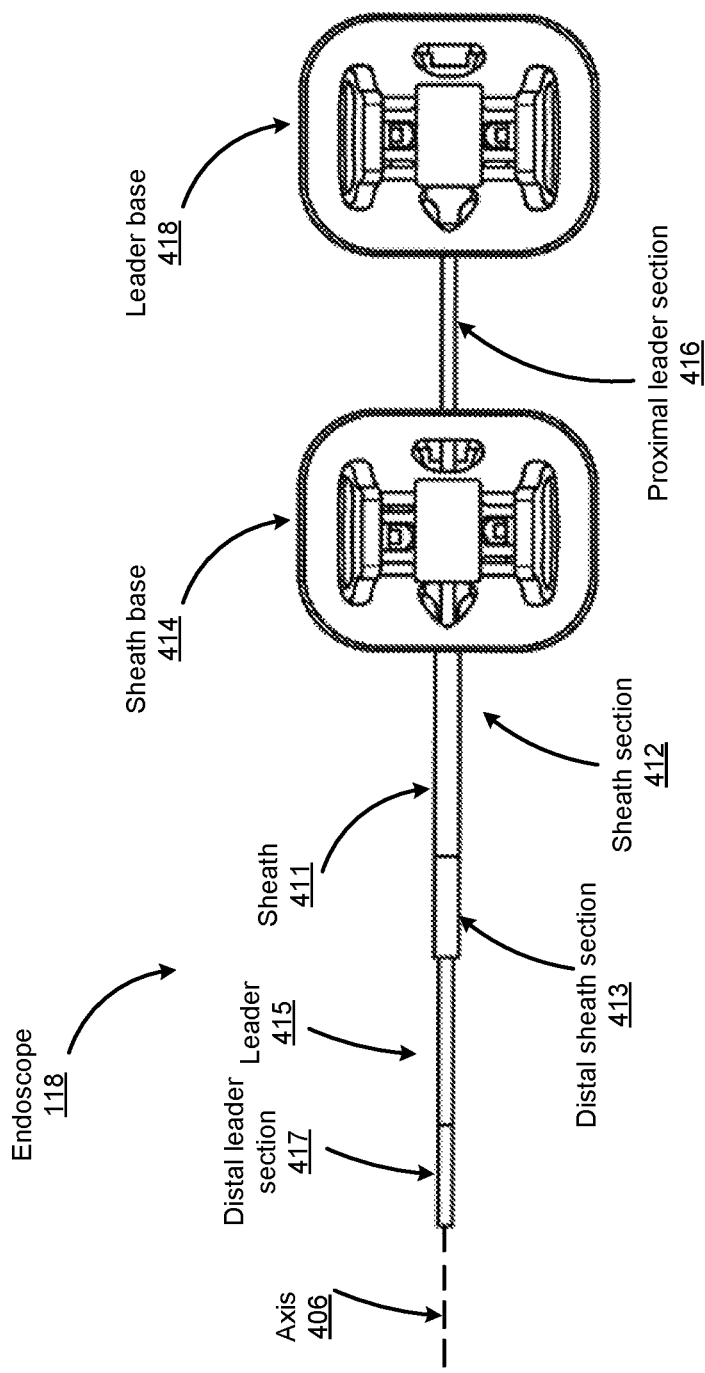

ENDOLUMENAL OBJECT SIZING

INCORPORATION BY REFERENCE TO ANY PRIORITY APPLICATIONS

This application is a continuation of U.S. patent application Ser. No. 16/179,568, filed Nov. 2, 2018, which is a continuation of U.S. patent application Ser. No. 15/392,674, filed Dec. 28, 2016, which is incorporated herein by reference. Any and all applications for which a foreign or domestic priority claim is identified in the Application Data Sheet as filed with the present application are hereby incorporated by reference by 37 C.F.R. 1.57.

BACKGROUND

1. Field of Art

This description generally relates to surgical robotics, and particularly to sizing an object within a lumen of a patient's body.

2. Description of the Related Art

In ureteroscopy, endoscopic removal of objects (e.g., kidney stones) within a patient's body often involves use of basket to capture of the kidney stone, retraction of the basket, and retraction of the ureteroscope down the ureter, bladder and out the urethra. During retraction of the basket and the ureteroscope, there is a risk that the kidney stone, being too large in diameter, may cause avulsion of the ureter. In conventional surgical systems, practitioners like physicians typically position an endolumenal safety wire to trace the path of the ureter from the bladder to the kidney in order to guide the reattachment of the ureter if the ureter is avulsed. The used of a safety wire, however, creates an additional step to the physician's workflow. In addition, kidney stones are not easily seen and measured using current external viewing techniques like fluoroscopy.

Thus, there is a need for a method of endolumenally measuring the size of a kidney stone in order to determine whether it is safe to retract the ureteroscope and endoscopically extract the kidney stone.

SUMMARY

The methods and systems disclosed herein allow for sizing an object positioned within a patient's body, for example, a kidney stone within a patient's ureter. As one example, an object sizing system sizes an object positioned within a patient. The object sizing system identifies a presence of the object. The object sizing system navigates an elongate body of an instrument to a position proximal to the object within the patient. An imaging sensor coupled to the elongate body captures one or more sequential images of the object. The instrument may be further moved around within the patient to capture additional images at different positions/orientations relative to the object. The object sizing system also acquires robot data and/or EM data associated with the positions and orientations of the elongate body. The object sizing system analyzes the captured images based on the acquired robot data to estimate a size of the object.

A variety of specific techniques (and associated system components) may be used to estimate the size of the object. As one example, the object sizing system generates a stitched image from multiple captured images to identify a structure of the object. As another example, a robotic basket may be used to capture the object for determining a size of the object. As a further example, structured light can be used to illuminate the object, and the object sizing system estimates a size of the object based on illumination patterns projected on the object.

BRIEF DESCRIPTION OF DRAWINGS

FIG. 4A shows a top view of an example endoscope, according to one embodiment.

Reference will now be made in detail to several embodiments, examples of which are illustrated in the accompanying figures. It is noted that wherever practicable similar or like reference numbers may be used in the figures and may indicate similar or like functionality. The figures depict embodiments of the described system (or method) for purposes of illustration only. One skilled in the art will readily recognize from the following description that alternative embodiments of the structures and methods illustrated herein may be employed without departing from the principles described herein.

DETAILED DESCRIPTION OF DRAWINGS

I. Surgical Robotic System

Figure 1A:
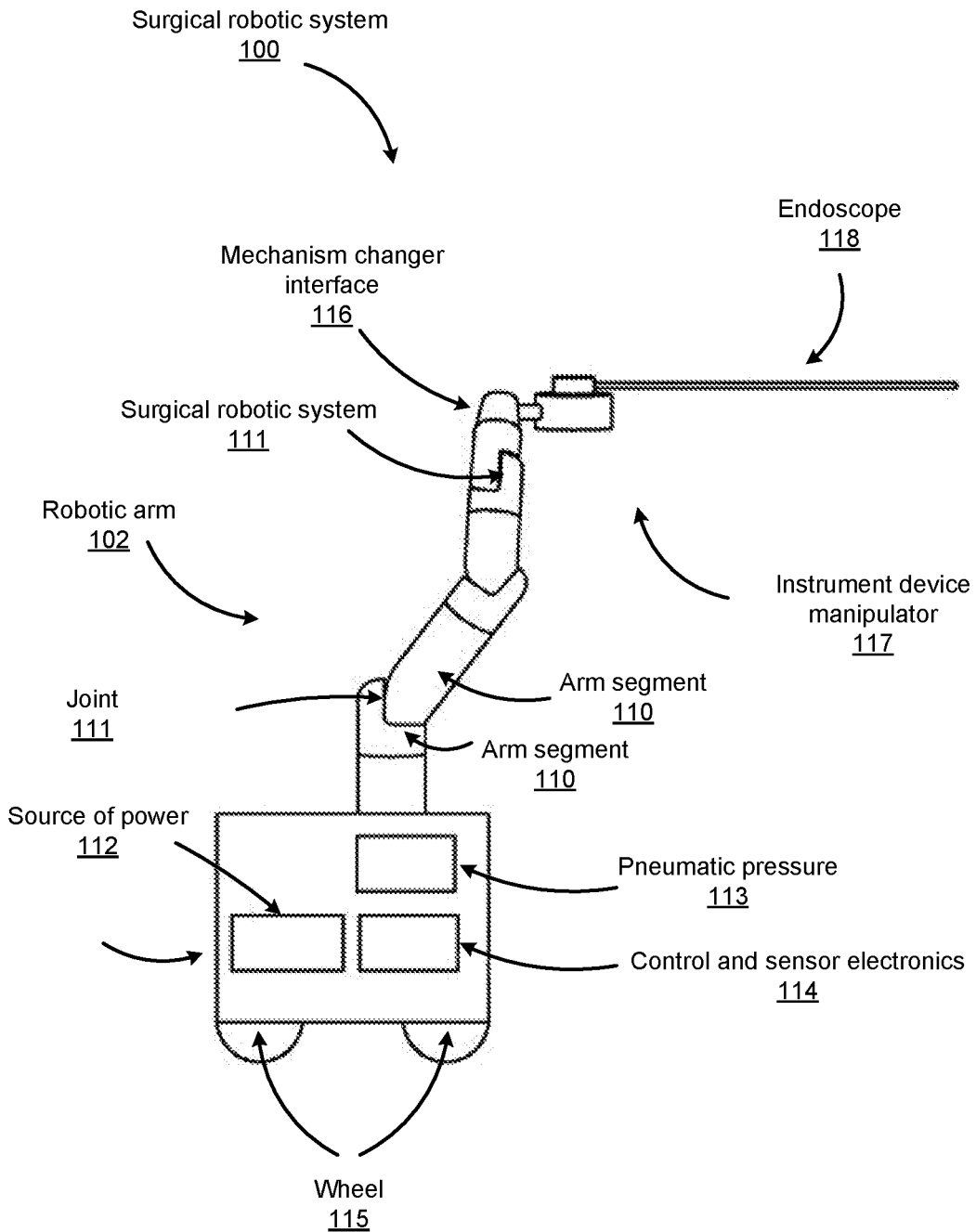
FIG. 1A shows an example surgical robotic system, according to one embodiment.

FIG. 1A shows an example surgical robotic system 100, according to one embodiment. The surgical robotic system 100 includes a base 101 coupled to one or more robotic arms, e.g., robotic arm 102. The base 101 is communicatively coupled to a command console, which is further described with reference to FIG. 2 in Section II. COMMAND CONSOLE. The base 101 can be positioned such that the robotic arm 102 has access to perform a surgical procedure on a patient, while a user such as a physician may control the surgical robotic system 100 from the comfort of the command console. In some embodiments, the base 101 may be coupled to a surgical operating table or bed for supporting the patient. Though not shown in FIG. 1 for purposes of clarity, the base 101 may include subsystems such as control electronics, pneumatics, power sources, optical sources, and the like. The robotic arm 102 includes multiple arm segments 110 coupled at joints 111, which provides the robotic arm 102 multiple degrees of freedom, e.g., seven degrees of freedom corresponding to seven arm segments. The base 101 may contain a source of power 112, pneumatic pressure 113, and control and sensor electronics 114—including components such as a central processing unit, data bus, control circuitry, and memory—and related actuators such as motors to move the robotic arm 102. The electronics 114 in the base 101 may also process and transmit control signals communicated from the command console.

In some embodiments, the base 101 includes wheels 115 to transport the surgical robotic system 100. Mobility of the surgical robotic system 100 helps accommodate space constraints in a surgical operating room as well as facilitate appropriate positioning and movement of surgical equipment. Further, the mobility allows the robotic arms 102 to be configured such that the robotic arms 102 do not interfere with the patient, physician, anesthesiologist, or any other equipment. During procedures, a user may control the robotic arms 102 using control devices such as the command console.

In some embodiments, the robotic arm 102 includes set up joints that use a combination of brakes and counter-balances to maintain a position of the robotic arm 102. The counter-balances may include gas springs or coil springs. The brakes, e.g., fail safe brakes, may be include mechanical and/or electrical components. Further, the robotic arms 102 may be gravity-assisted passive support type robotic arms.

Each robotic arm 102 may be coupled to a robotic manipulator like an instrument device manipulator (IDM) 117 using a mechanism changer interface (MCI) 116. The IDM 117 can be removed and replaced with a different type of IDM, for example, a first type of IDM manipulates an endoscope, while a second type of IDM manipulates a laparoscope. The MCI 116 includes connectors to transfer pneumatic pressure, electrical power, electrical signals, and optical signals from the robotic arm 102 to the IDM 117. The MCI 116 can be a set screw or base plate connector. The IDM 117 manipulates surgical instruments such as the endoscope 118 using techniques including direct drive, harmonic drive, geared drives, belts and pulleys, magnetic drives, and the like. The MCI 116 is interchangeable based on the type of IDM 117 and can be customized for a certain type of surgical procedure. The robotic 102 arm can include a joint level torque sensing and a wrist at a distal end, such as the KUKA AG® LBR5 robotic arm. [0046] The endoscope 118 is a tubular and flexible surgical instrument that is inserted into the anatomy of a patient to capture images of the anatomy (e.g., body tissue). In particular, the endoscope 118 includes one or more imaging devices (e.g., cameras or other types of imaging sensors) that capture the images. The imaging devices may include one or more optical components such as an optical fiber, fiber array, or lens. The optical components move along with the tip of the endoscope 118 such that movement of the tip of the endoscope 118 results in changes to the images captured by the imaging devices. The endoscope 118 is further described with reference to FIGS. 3A-4B in Section IV. Endoscope.

Robotic arms 102 of the surgical robotic system 100 manipulate the endoscope 118 using elongate movement members. The elongate movement members may include pull wires, also referred to as pull or push wires, cables, fibers, or flexible shafts. For example, the robotic arms 102 actuate multiple pull wires coupled to the endoscope 118 to deflect the tip of the endoscope 118. The pull wires may include both metallic and non-metallic materials such as stainless steel, Kevlar, tungsten, carbon fiber, and the like. The endoscope 118 may exhibit nonlinear behavior in response to forces applied by the elongate movement members. The nonlinear behavior may be based on stiffness and compressibility of the endoscope 118, as well as variability in slack or stiffness between different elongate movement members.

Figure 1B:
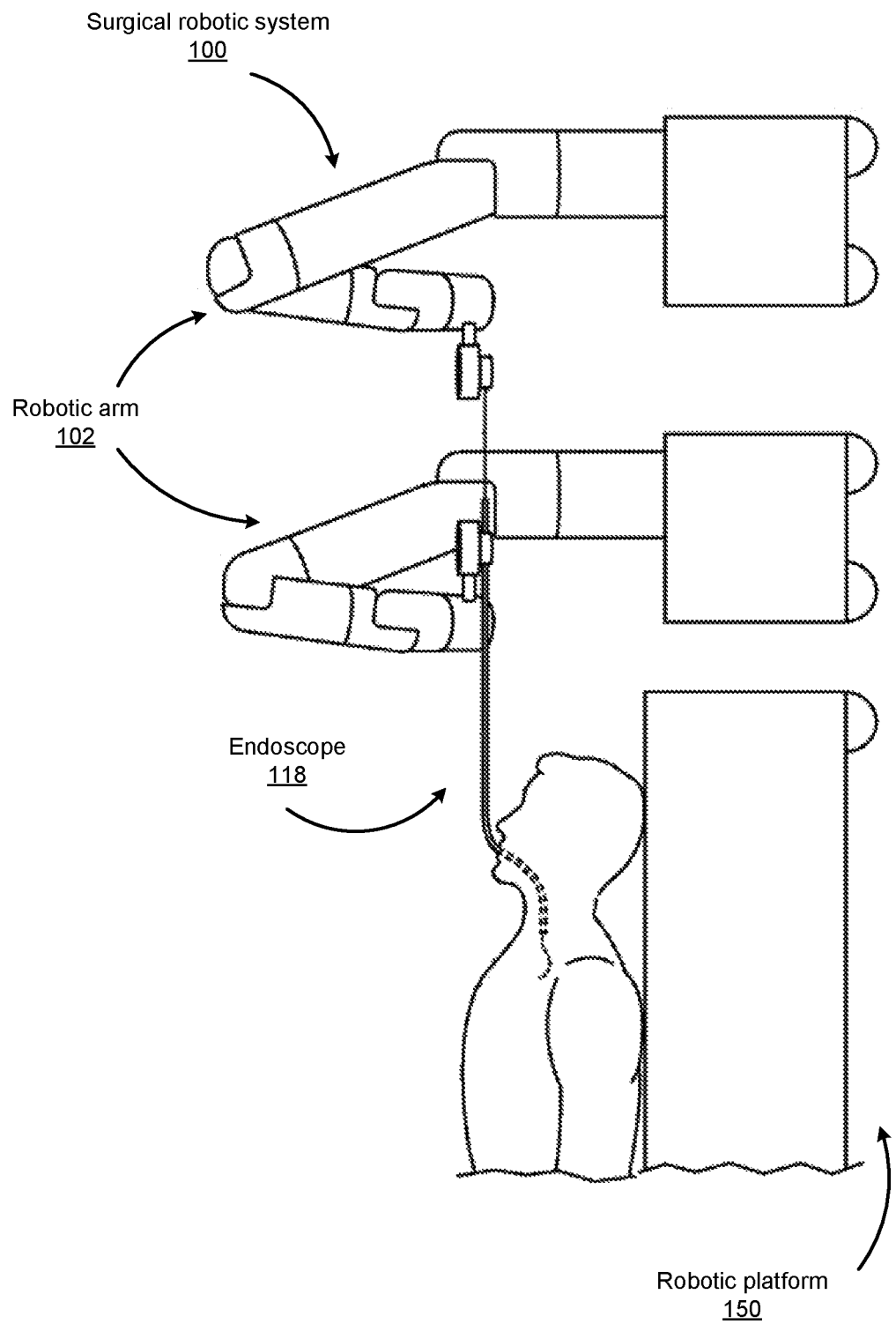
FIGS. 1B-1F show various perspective views of a robotic platform coupled to the surgical robotic system shown in FIG. 1A, according to one embodiment.
Figure 1C:
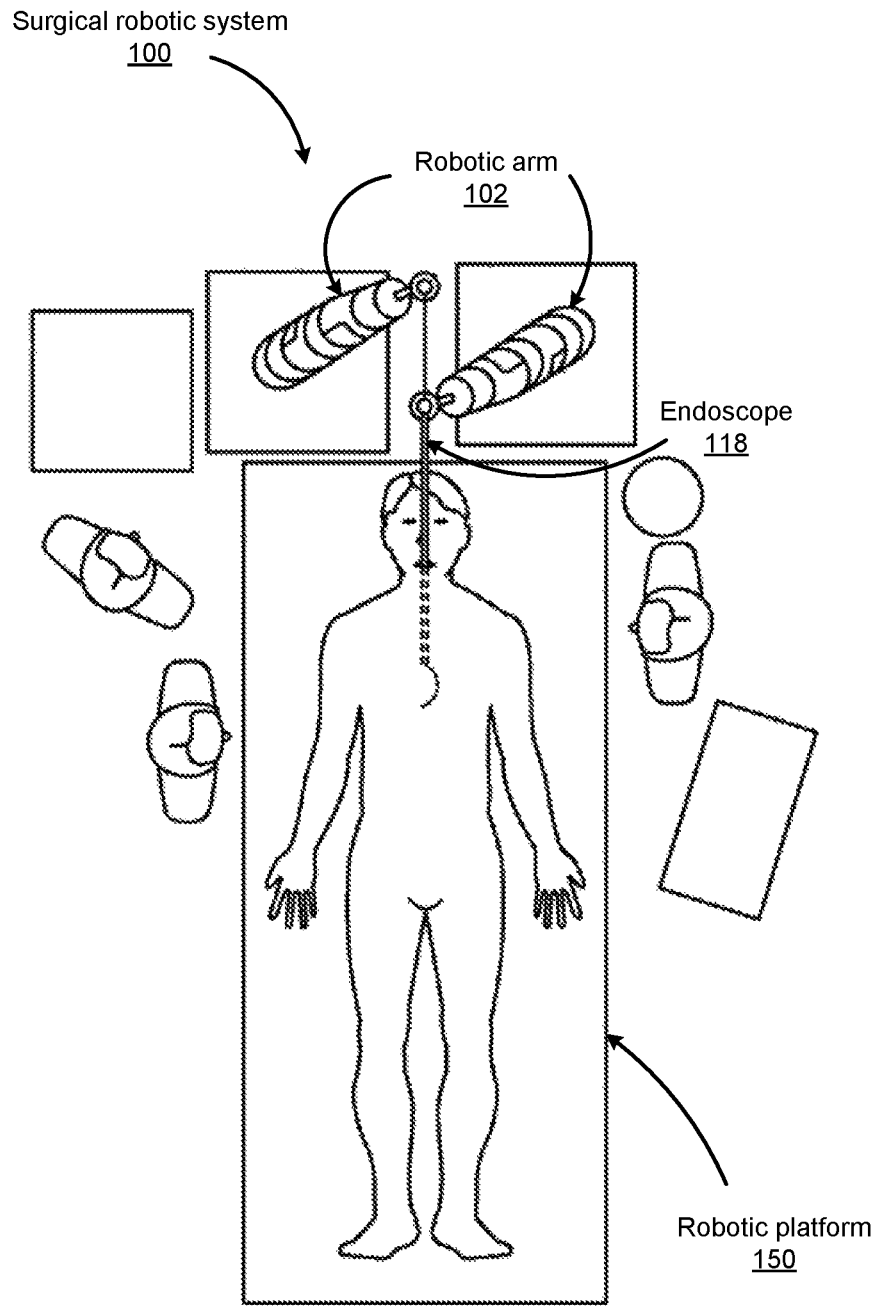
Figure 1D:
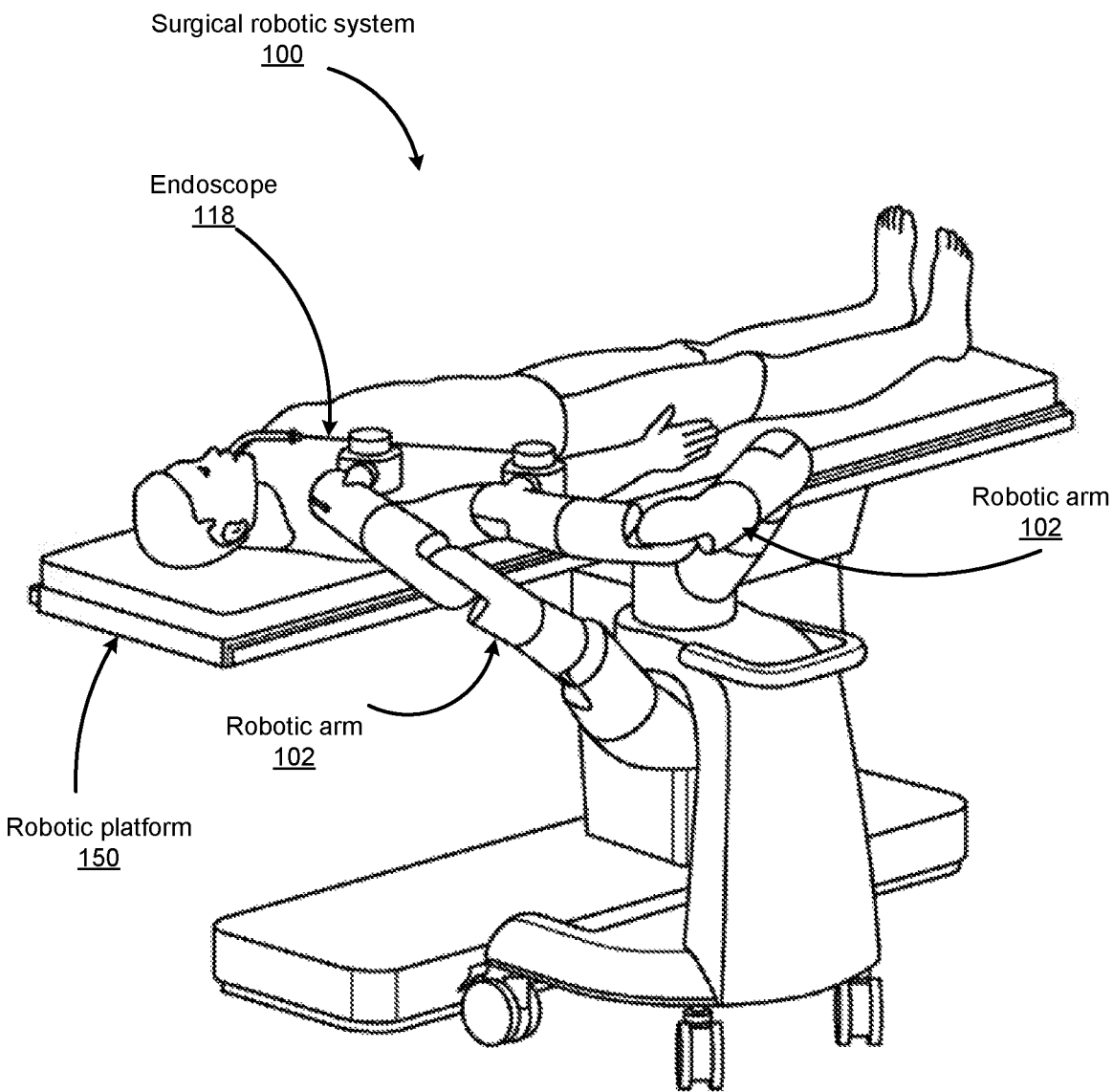
Figure 1E:
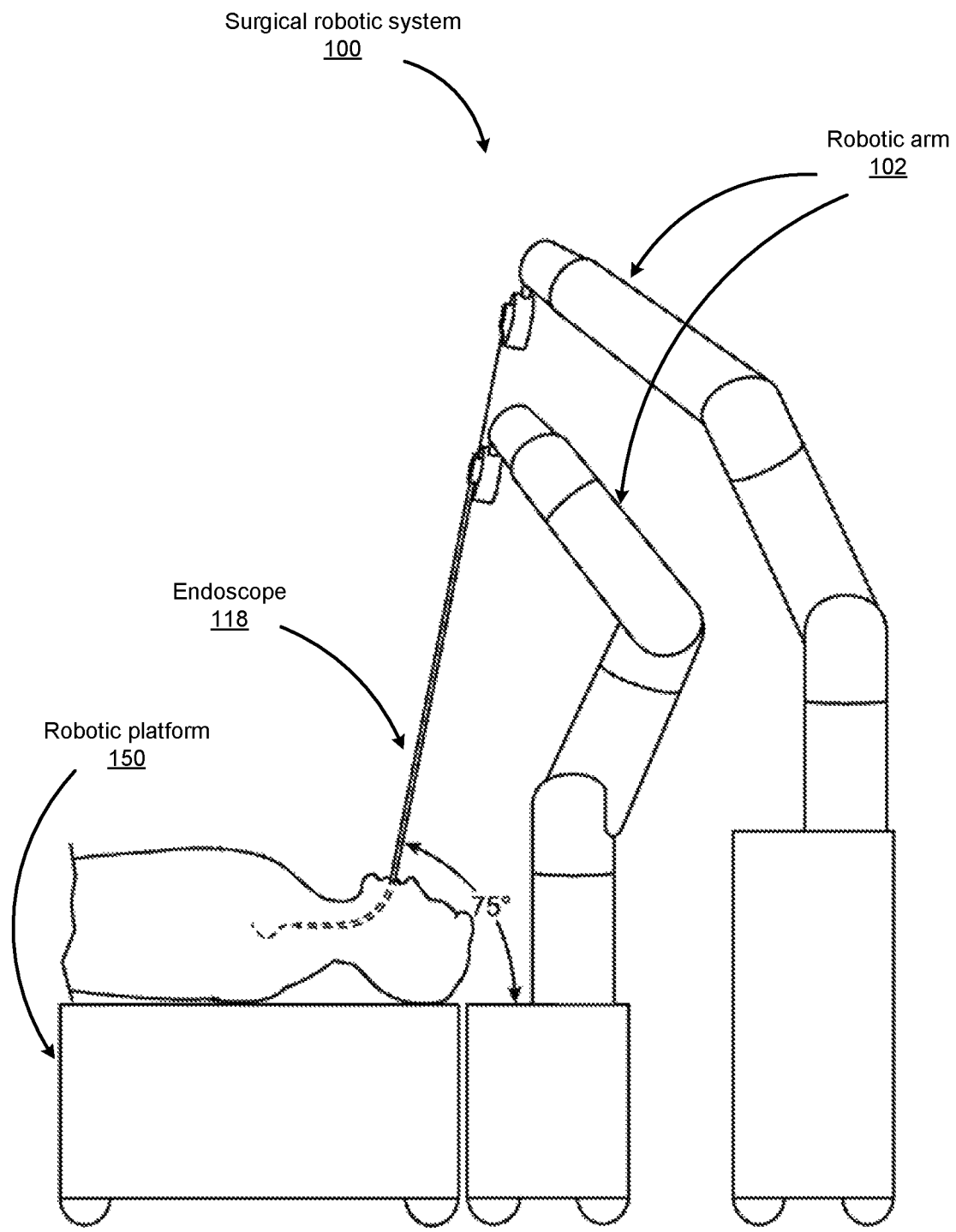
Figure 1F:
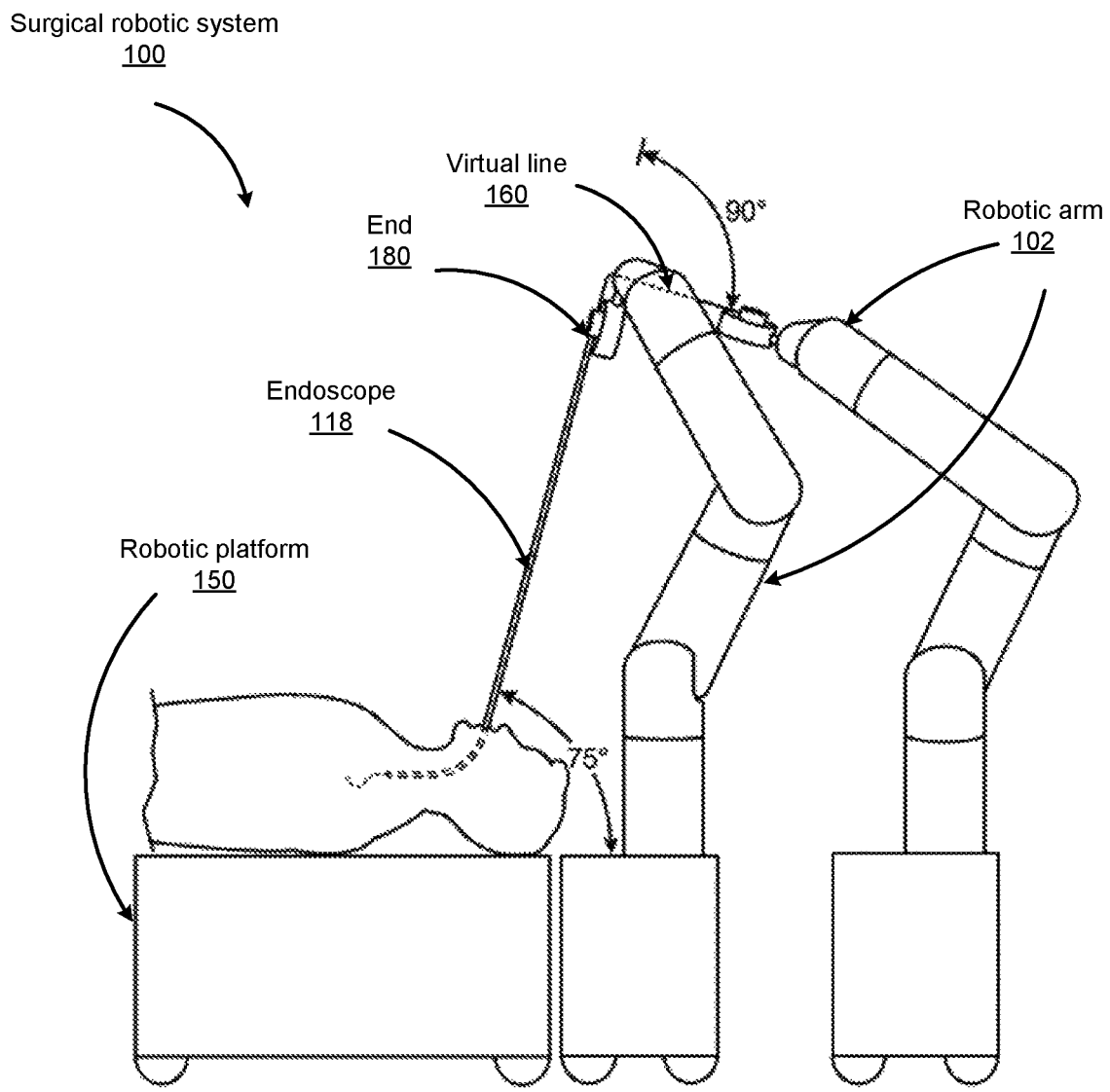

FIGS. 1B-1F show various perspective views of the surgical robotic system 100 coupled to a robotic platform 150 (or surgical bed), according to various embodiments. Specifically, FIG. 1B shows a side view of the surgical robotic system 100 with the robotic arms 102 manipulating the endoscopic 118 to insert the endoscopic inside a patient's body, and the patient is lying on the robotic platform 150. FIG. 1C shows a top view of the surgical robotic system 100 and the robotic platform 150, and the endoscopic 118 manipulated by the robotic arms is inserted inside the patient's body. FIG. 1D shows a perspective view of the surgical robotic system 100 and the robotic platform 150, and the endoscopic 118 is controlled to be positioned horizontally parallel with the robotic platform. FIG. 1E shows another perspective view of the surgical robotic system 100 and the robotic platform 150, and the endoscopic 118 is controlled to be positioned relatively perpendicular to the robotic platform. In more detail, in FIG. 1E, the angle between the horizontal surface of the robotic platform 150 and the endoscopic 118 is 75 degree. FIG. 1F shows the perspective view of the surgical robotic system 100 and the robotic platform 150 shown in FIG. 1E, and in more detail, the angle between the endoscopic 118 and the virtual line 160 connecting one end 180 of the endoscopic and the robotic arm 102 that is positioned relatively farther away from the robotic platform is 90 degree.

II. Command Console

Figure 2:
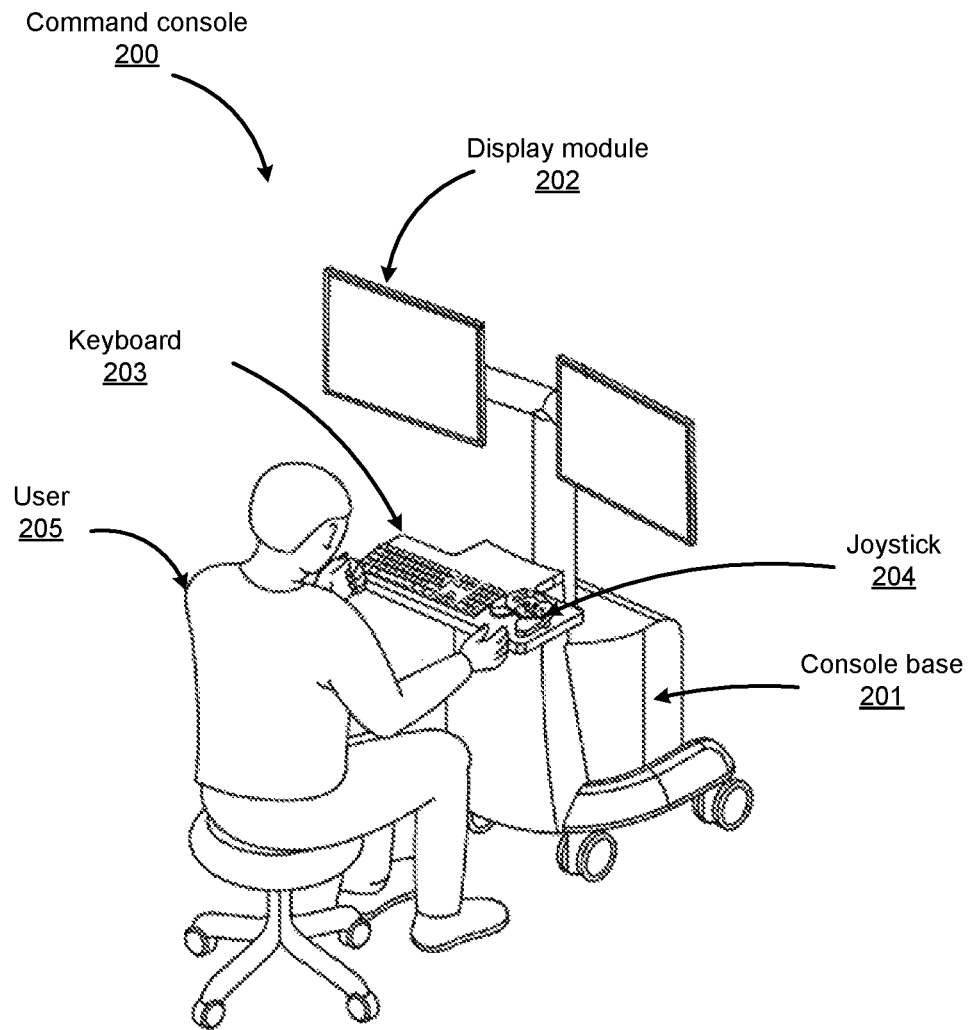
FIG. 2 shows an example command console for the example surgical robotic system, according to one embodiment.

FIG. 2 shows an example command console 200 for the example surgical robotic system 100, according to one embodiment. The command console 200 includes a console base 201, display modules 202, e.g., monitors, and control modules, e.g., a keyboard 203 and joystick 204. In some embodiments, one or more of the command console 200 functionality may be integrated into a base 101 of the surgical robotic system 100 or another system communicatively coupled to the surgical robotic system 100. A user 205, e.g., a physician, remotely controls the surgical robotic system 100 from an ergonomic position using the command console 200.

The console base 201 may include a central processing unit, a memory unit, a data bus, and associated data communication ports that are responsible for interpreting and processing signals such as camera imagery and tracking sensor data, e.g., from the endoscope 118 shown in FIG. 1. In some embodiments, both the console base 201 and the base 101 perform signal processing for load-balancing. The console base 201 may also process commands and instructions provided by the user 205 through the control modules 203 and 204. In addition to the keyboard 203 and joystick 204 shown in FIG. 2, the control modules may include other devices, for example, computer mice, trackpads, trackballs, control pads, video game controllers, and sensors (e.g., motion sensors or cameras) that capture hand gestures and finger gestures.

The user 205 can control a surgical instrument such as the endoscope 118 using the command console 200 in a velocity mode or position control mode. In velocity mode, the user 205 directly controls pitch and yaw motion of a distal end of the endoscope 118 based on direct manual control using the control modules. For example, movement on the joystick 204 may be mapped to yaw and pitch movement in the distal end of the endoscope 118. The joystick 204 can provide haptic feedback to the user 205. For example, the joystick 204 vibrates to indicate that the endoscope 118 cannot further translate or rotate in a certain direction. The command console 200 can also provide visual feedback (e.g., pop-up messages) and/or audio feedback (e.g., beeping) to indicate that the endoscope 118 has reached maximum translation or rotation.

In position control mode, the command console 200 uses a three-dimensional (3D) map of a patient and pre-determined computer models of the patient to control a surgical instrument, e.g., the endoscope 118. The command console 200 provides control signals to robotic arms 102 of the surgical robotic system 100 to manipulate the endoscope 118 to a target location. Due to the reliance on the 3D map, position control mode requires accurate mapping of the anatomy of the patient.

In some embodiments, users 205 can manually manipulate robotic arms 102 of the surgical robotic system 100 without using the command console 200. During setup in a surgical operating room, the users 205 may move the robotic arms 102, endoscopes 118, and other surgical equipment to access a patient. The surgical robotic system 100 may rely on force feedback and inertia control from the users 205 to determine appropriate configuration of the robotic arms 102 and equipment.

The display modules 202 may include electronic monitors, virtual reality viewing devices, e.g., goggles or glasses, and/or other means of display devices. In some embodiments, the display modules 202 are integrated with the control modules, for example, as a tablet device with a touchscreen. Further, the user 205 can both view data and input commands to the surgical robotic system 100 using the integrated display modules 202 and control modules.

The display modules 202 can display 3D images using a stereoscopic device, e.g., a visor or goggle. The 3D images provide an "endo view" (i.e., endoscopic view), which is a computer 3D model illustrating the anatomy of a patient. The "endo view" provides a virtual environment of the patient's interior and an expected location of an endoscope 118 inside the patient. A user 205 compares the "endo view" model to actual images captured by a camera to help mentally orient and confirm that the endoscope 118 is in the correct—or approximately correct—location within the patient. The "endo view" provides information about anatomical structures, e.g., the shape of an intestine or colon of the patient, around the distal end of the endoscope 118. The display modules 202 can simultaneously display the 3D model and computerized tomography (CT) scans of the anatomy the around distal end of the endoscope 118. Further, the display modules 202 may overlay the already determined navigation paths of the endoscope 118 on the 3D model and CT scans.

In some embodiments, a model of the endoscope 118 is displayed with the 3D models to help indicate a status of a surgical procedure. For example, the CT scans identify a lesion in the anatomy where a biopsy may be necessary. During operation, the display modules 202 may show a reference image captured by the endoscope 118 corresponding to the current location of the endoscope 118. The display modules 202 may automatically display different views of the model of the endoscope 118 depending on user settings and a particular surgical procedure. For example, the display modules 202 show an overhead fluoroscopic view of the endoscope 118 during a navigation step as the endoscope 118 approaches an operative region of a patient.

III. Instrument Device Manipulator

Figure 3A:
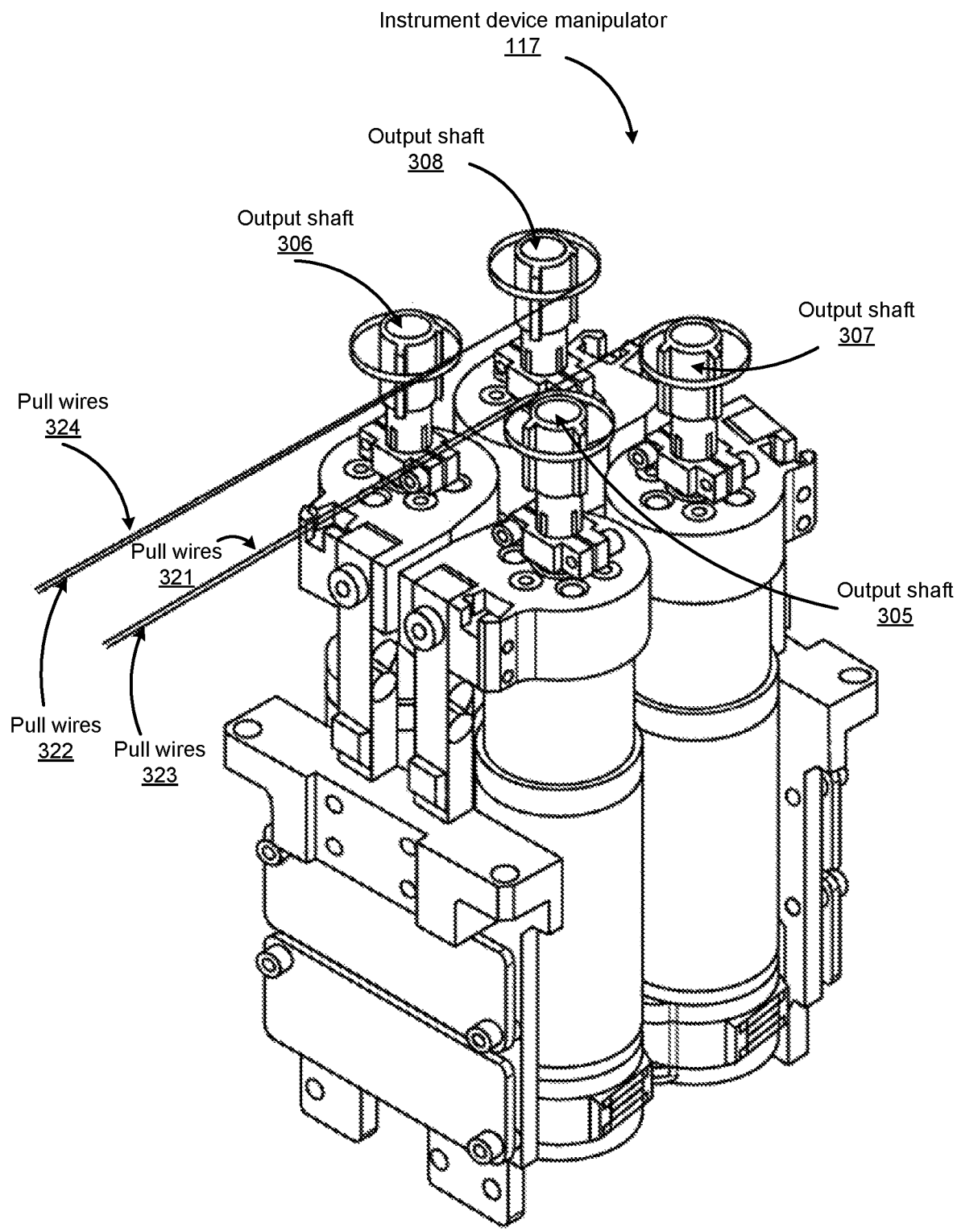
FIG. 3A shows an isometric view of an example independent drive mechanism of the instrument device manipulator (IDM) shown in FIG. 1A, according to one embodiment.

FIG. 3A shows an isometric view of an example independent drive mechanism of the IDM 117 shown in FIG. 1, according to one embodiment. The independent drive mechanism can tighten or loosen the pull wires 321, 322, 323, and 324 (e.g., independently from each other) of an endoscope by rotating the output shafts 305, 306, 307, and 308 of the IDM 117, respectively. Just as the output shafts 305, 306, 307, and 308 transfer force down pull wires 321, 322, 323, and 324, respectively, through angular motion, the pull wires 321, 322, 323, and 324 transfer force back to the output shafts. The IDM 117 and/or the surgical robotic system 100 can measure the transferred force using a sensor, e.g., a strain gauge further described below.

Figure 3B:
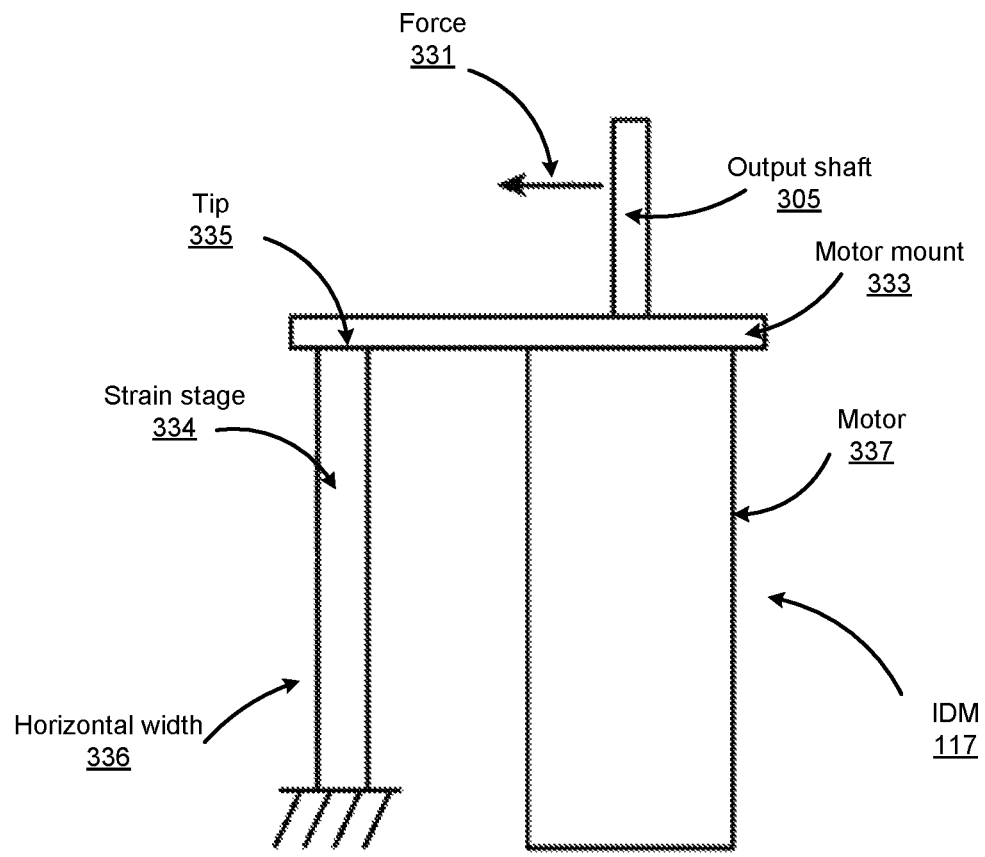
FIG. 3B shows a conceptual diagram that shows how forces may be measured by a strain gauge of the independent drive mechanism shown in FIG. 3A, according to one embodiment.

FIG. 3B shows a conceptual diagram that shows how forces may be measured by a strain gauge 334 of the independent drive mechanism shown in FIG. 3A, according to one embodiment. A force 331 may direct away from the output shaft 305 coupled to the motor mount 333 of the motor 337. Accordingly, the force 331 results in horizontal displacement of the motor mount 333. Further, the strain gauge 334 horizontally coupled to the motor mount 333 experiences strain in the direction of the force 331. The strain may be measured as a ratio of the horizontal displacement of the tip 335 of strain gauge 334 to the overall horizontal width 336 of the strain gauge 334.

In some embodiments, the IDM 117 includes additional sensors, e.g., inclinometers or accelerometers, to determine an orientation of the IDM 117. Based on measurements from the additional sensors and/or the strain gauge 334, the surgical robotic system 100 can calibrate readings from the strain gauge 334 to account for gravitational load effects. For example, if the IDM 117 is oriented on a horizontal side of the IDM 117, the weight of certain components of the IDM 117 may cause a strain on the motor mount 333. Accordingly, without accounting for gravitational load effects, the strain gauge 334 may measure strain that did not result from strain on the output shafts.

IV. Endoscope

FIG. 4A shows a top view of an example endoscope 118, according to one embodiment. The endoscope 118 includes a leader 415 tubular component nested or partially nested inside and longitudinally-aligned with a sheath 411 tubular component. The sheath 411 includes a proximal sheath section 412 and distal sheath section 413. The leader 415 has a smaller outer diameter than the sheath 411 and includes a proximal leader section 416 and distal leader section 417. The sheath base 414 and the leader base 418 actuate the distal sheath section 413 and the distal leader section 417, respectively, for example, based on control signals from a user of a surgical robotic system 100. The sheath base 414 and the leader base 418 are, e.g., part of the IDM 117 shown in FIG. 1.

Both the sheath base 414 and the leader base 418 include drive mechanisms (e.g., the independent drive mechanism further described with reference to FIG. 3A-B in Section III. Instrument Device Manipulator) to control pull wires coupled to the sheath 411 and leader 415. For example, the sheath base 414 generates tensile loads on pull wires coupled to the sheath 411 to deflect the distal sheath section 413. Similarly, the leader base 418 generates tensile loads on pull wires coupled to the leader 415 to deflect the distal leader section 417. Both the sheath base 414 and leader base 418 may also include couplings for the routing of pneumatic pressure, electrical power, electrical signals, or optical signals from IDMs to the sheath 411 and leader 414, respectively. A pull wire may include a steel coil pipe along the length of the pull wire within the sheath 411 or the leader 415, which transfers axial compression back to the origin of the load, e.g., the sheath base 414 or the leader base 418, respectively.

The endoscope 118 can navigate the anatomy of a patient with ease due to the multiple degrees of freedom provided by pull wires coupled to the sheath 411 and the leader 415. For example, four or more pull wires may be used in either the sheath 411 and/or the leader 415, providing eight or more degrees of freedom. In other embodiments, up to three pull wires may be used, providing up to six degrees of freedom. The sheath 411 and leader 415 may be rotated up to 360 degrees along a longitudinal axis 406, providing more degrees of motion. The combination of rotational angles and multiple degrees of freedom provides a user of the surgical robotic system 100 with a user friendly and instinctive control of the endoscope 118.

Figure 4B:
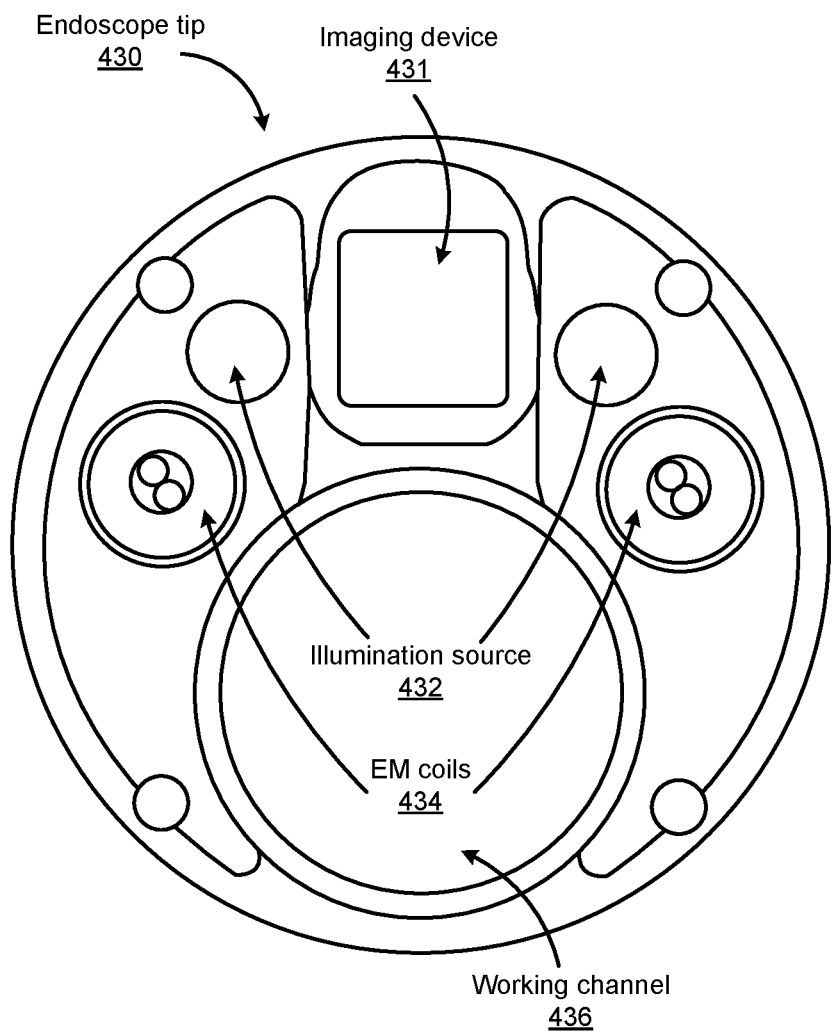
FIG. 4B shows an example endoscope tip of the endoscope shown in FIG. 4A, according to one embodiment.

FIG. 4B illustrates an example endoscope tip 430 of the endoscope 118 shown in FIG. 4A, according to one embodiment. In FIG. 4B, the endoscope tip 430 includes an imaging device 431 (e.g., a camera), illumination sources 432, and one or more electromagnetic (EM) coils 434 (also referred to as EM sensors). The illumination sources 432 provide light to illuminate an interior portion of an anatomical space. The provided light allows the imaging device 431 to record images of that space, which can then be transmitted to a computer system such as command console 200 for processing as described herein. EM coils 434 located on the tip 430 may be used with an electromagnetic tracking system to detect the position and orientation of the endoscope tip 430 while it is disposed within an anatomical system. In some embodiments, the coils may be angled to provide sensitivity to electromagnetic fields along different axes, giving the ability to measure a full 6 degrees of freedom: three positional and three angular. In other embodiments, only a single coil may be disposed within the endoscope tip 430, with its axis oriented along the endoscope shaft of the endoscope 118; due to the rotational symmetry of such a system, it is insensitive to roll about its axis, so only 5 degrees of freedom may be detected in such a case. The endoscope tip 430 further comprises a working channel 436 through which surgical instruments, such as biopsy needles, may be inserted along the endoscope shaft, allowing access to the area near the endoscope tip.

The principles described in the above application are also applicable to catheter designs. Generally, although the preceding and following sections of this description describe endoscope embodiments, this is merely one example, and the description that follows can also be implemented and/or used in conjunction with catheters as well, or more generally any flexible instrument comprising an elongate body.

V. Registration Transform of EM System to 3D Model

V. A. Schematic Setup of an EM Tracking System

Figure 5A:
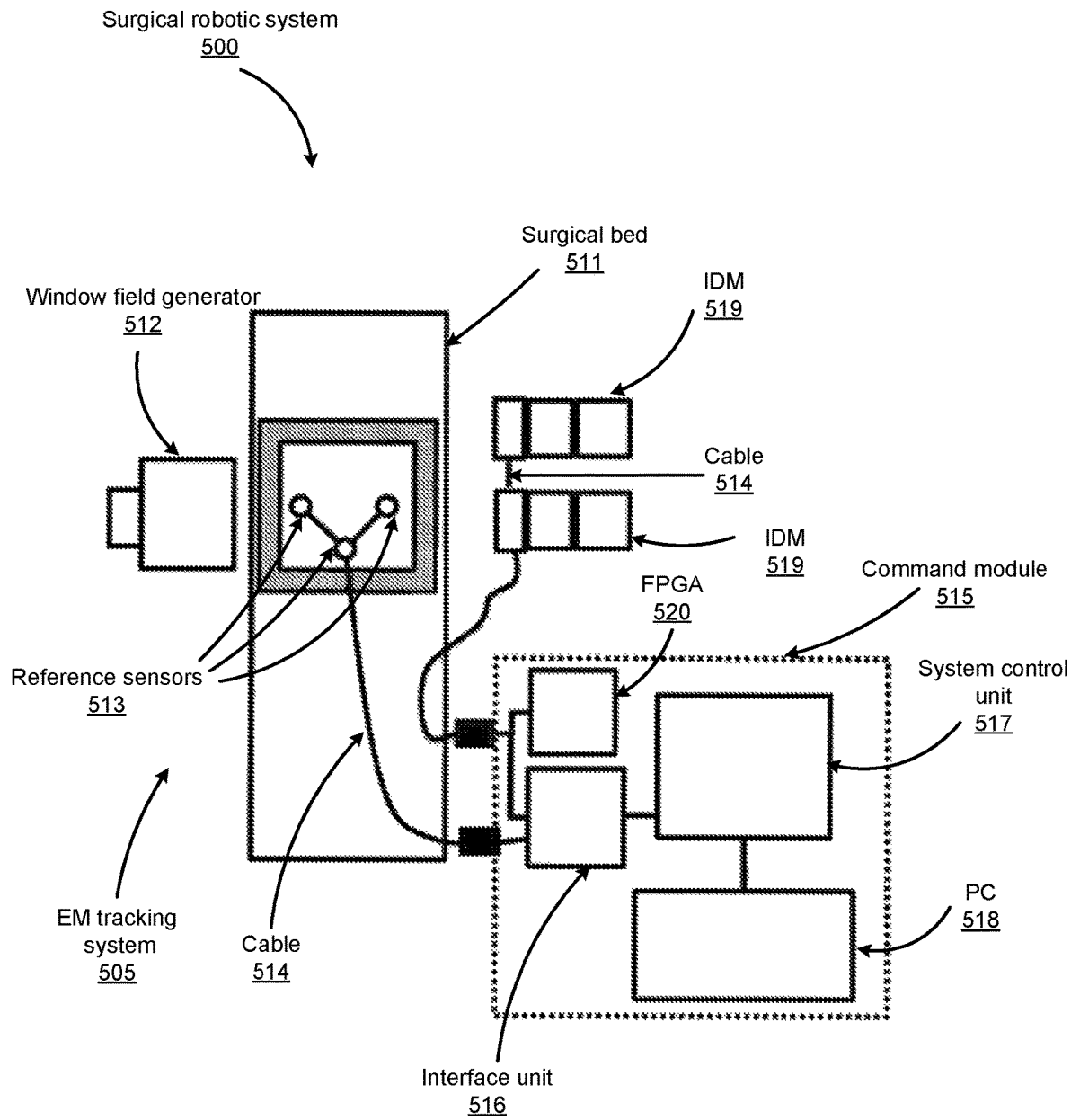
FIG. 5A shows an example schematic setup of an EM tracking system included in a surgical robotic system, according to one embodiment.

FIG. 5A shows an example schematic setup of an EM tracking system 505 included in a surgical robotic system 500, according to one embodiment. In FIG. 5A, multiple robot components (e.g., window field generator, reference sensors as described below) are included in the EM tracking system 505. The robotic surgical system 500 includes a surgical bed 511 to hold a patient's body. Beneath the bed 511 is the window field generator (WFG) 512 configured to sequentially activate a set of EM coils (e.g., the EM coils 434 shown in FIG. 4B). The WFG 512 generates an alternating current (AC) magnetic field over a wide volume; for example, in some cases it may create an AC field in a volume of about 0.5×0.5×0.5 m.

Additional fields may be applied by further field generators to aid in tracking instruments within the body. For example, a planar field generator (PFG) may be attached to a system arm adjacent to the patient and oriented to provide an EM field at an angle. Reference sensors 513 may be placed on the patient's body to provide local EM fields to further increase tracking accuracy. Each of the reference sensors 513 may be attached by cables 514 to a command module 515. The cables 514 are connected to the command module 515 through interface units 516 which handle communications with their respective devices as well as providing power. The interface unit 516 is coupled to a system control unit (SCU) 517 which acts as an overall interface controller for the various entities mentioned above. The SCU 517 also drives the field generators (e.g., WFG 512), as well as collecting sensor data from the interface units 516, from which it calculates the position and orientation of sensors within the body. The SCU 517 may be coupled to a personal computer (PC) 518 to allow user access and control.

The command module 515 is also connected to the various IDMs 519 coupled to the surgical robotic system 500 as described herein. The IDMs 519 are typically coupled to a single surgical robotic system (e.g., the surgical robotic system 500) and are used to control and receive data from their respective connected robotic components; for example, robotic endoscope tools or robotic arms. As described above, as an example, the IDMs 519 are coupled to an endoscopic tool (not shown here) of the surgical robotic system 500

The command module 515 receives data passed from the endoscopic tool. The type of received data depends on the corresponding type of instrument attached. For example, example received data includes sensor data (e.g., image data, EM data), robot data (e.g., endoscopic and IDM physical motion data), control data, and/or video data. To better handle video data, a field-programmable gate array (FPGA) 520 may be configured to handle image processing. Comparing data obtained from the various sensors, devices, and field generators allows the SCU 517 to precisely track the movements of different components of the surgical robotic system 500, and for example, positions and orientations of these components.

In order to track a sensor through the patient's anatomy, the EM tracking system 505 may require a process known as "registration," where the system finds the geometric transformation that aligns a single object between different coordinate systems. For instance, a specific anatomical site on a patient has two different representations in the 3D model coordinates and in the EM sensor coordinates. To be able to establish consistency and common language between these two different coordinate systems, the EM tracking system 505 needs to find the transformation that links these two representations, i.e., registration. For example, the position of the EM tracker relative to the position of the EM field generator may be mapped to a 3D coordinate system to isolate a location in a corresponding 3D model.

V. C. On-the-Fly Electromagnetic Registration

Figure 5B:
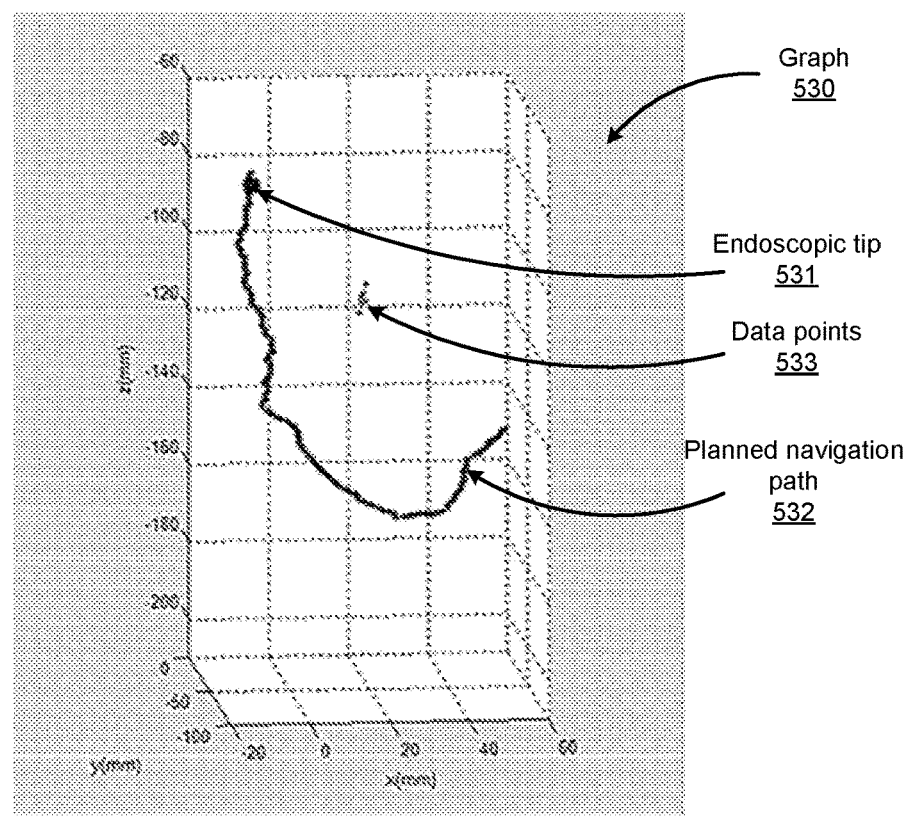
FIGS. 5B-5E show example graphs illustrating on-the-fly registration of an EM system to a 3D model of a path through a tubular network, according to one embodiment.

FIGS. 5B-5E show example graphs 510-540 illustrating on-the-fly registration of an EM system to a 3D model of a path through a tubular network, according to one embodiment. The navigation configuration system described herein allows for on-the-fly registration of the EM coordinates to the 3D model coordinates without the need for independent registration prior to an endoscopic procedure. In more detail, FIG. 5A shows that the coordinate systems of the EM tracking system and the 3D model are initially not registered to each other, and the graph 530 in FIG. 5A shows the registered location of an endoscope tip 531 moving along a planned navigation path 532 through a branched tubular network (not shown here), and the location of the instrument tip 531 as well as the planned path 532 are derived from the 3D model. The location of the endoscopic tip 531 shown in FIG. 5B is an expected location derived from the 3D model rather than the actual location of the tip. The actual position of the tip is repeatedly measured by the EM tracking system 505, resulting in multiple measured location data points 533 based on EM data. As shown in FIG. 5B, the data points 533 derived from EM tracking are initially located far from the position of the endoscope tip 531 expected from the 3D model, reflecting the lack of registration between the EM coordinates and the 3D model coordinates. There may be several reasons for this, for example, even if the endoscope tip is being moved relatively smoothly through the tubular network, there may still be some visible scatter in the EM measurement, due to breathing movement of the lungs of the patient.

The points on the 3D model may also be determined and adjusted based on correlation between the 3D model itself, image data received from imaging sensors (e.g., cameras) and robot data from robot commands. The 3D transformation between these points and collected EM data points will determine the initial registration of the EM coordinate system to the 3D model coordinate system.

Figure 5C:
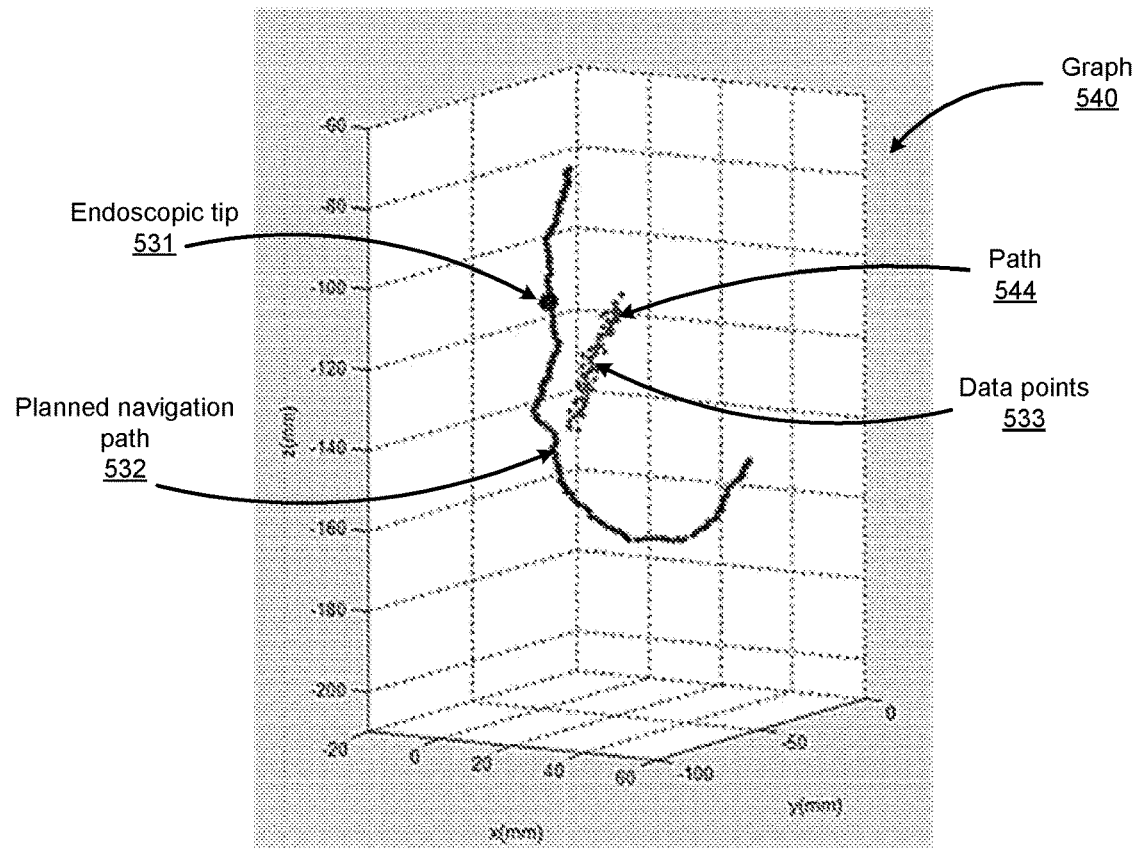

FIG. 5C shows a graph 540 at a later temporal stage compared with the graph 530, according to one embodiment. More specifically, the graph 540 shows the endoscope tip 531 expected from the 3D model has been moved farther along the preplanned navigation path 532, as illustrated by the shift from the original position of the instrument tip 531 shown in FIG. 5B along the path to the position shown in FIG. 5C. During the EM tracking between generation of the graph 530 and generation of graph 540, additional data points 533 have been recorded by the EM tracking system but the registration has not yet been updated based on the newly collected EM data. As a result, the data points 533 in FIG. 5C are clustered along a visible path 544, but that path differs in location and orientation from the planned navigation path 532 the endoscope tip is being directed by the operator to travel along. Eventually, once sufficient data (e.g., EM data) is accumulated, compared with using only the 3D model or only the EM data, a relatively more accurate estimate can be derived from the transform needed to register the EM coordinates to those of the 3D model. The determination of sufficient data may be made by threshold criteria such as total data accumulated or number of changes of direction. For example, in a branched tubular network such as a bronchial tube network, it may be judged that sufficient data have been accumulated after arriving at two branch points.

Figure 5D:
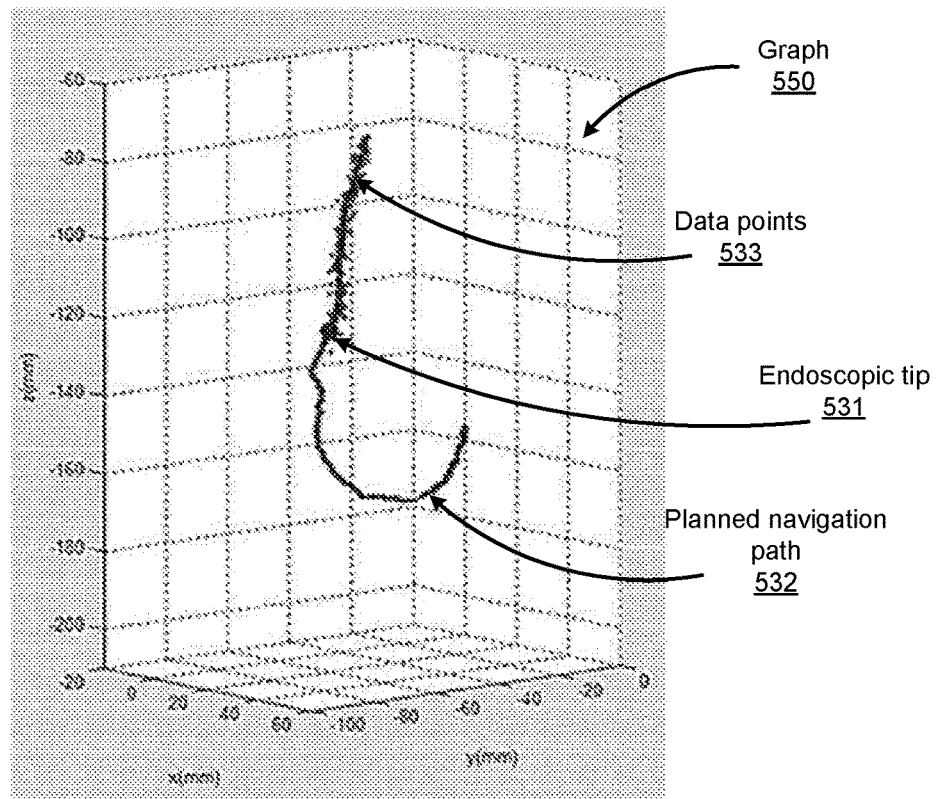

FIG. 5D shows a graph 550 shortly after the navigation configuration system has accumulated a sufficient amount of data to estimate the registration transform from EM to 3D model coordinates, according to one embodiment. The data points 533 in FIG. 5D have now shifted from their previous position as shown in FIG. 5C as a result of the registration transform. As shown in FIG. 5D, the data points 533 derived from EM data is now falling along the planned navigation path 532 derived from the 3D model, and each data point among the data points 533 is now reflecting a measurement of the position of endoscope tip 531 in the coordinate system of the 3D model, and as introduced above in FIGS. 5B-5C, the position of the tip 531 shown in FIG. 5D is an expected location derived from the 3D model rather than an actual location of the tip. In some embodiments, as further data are collected, the registration transform may be updated to increase accuracy. In some cases, the data used to determine the registration transformation may be a subset of data chosen by a moving window, so that the registration may change over time, which gives the ability to account for changes in the relative coordinates of the EM and 3D models—for example, due to movement of the patient.

Figure 5E:
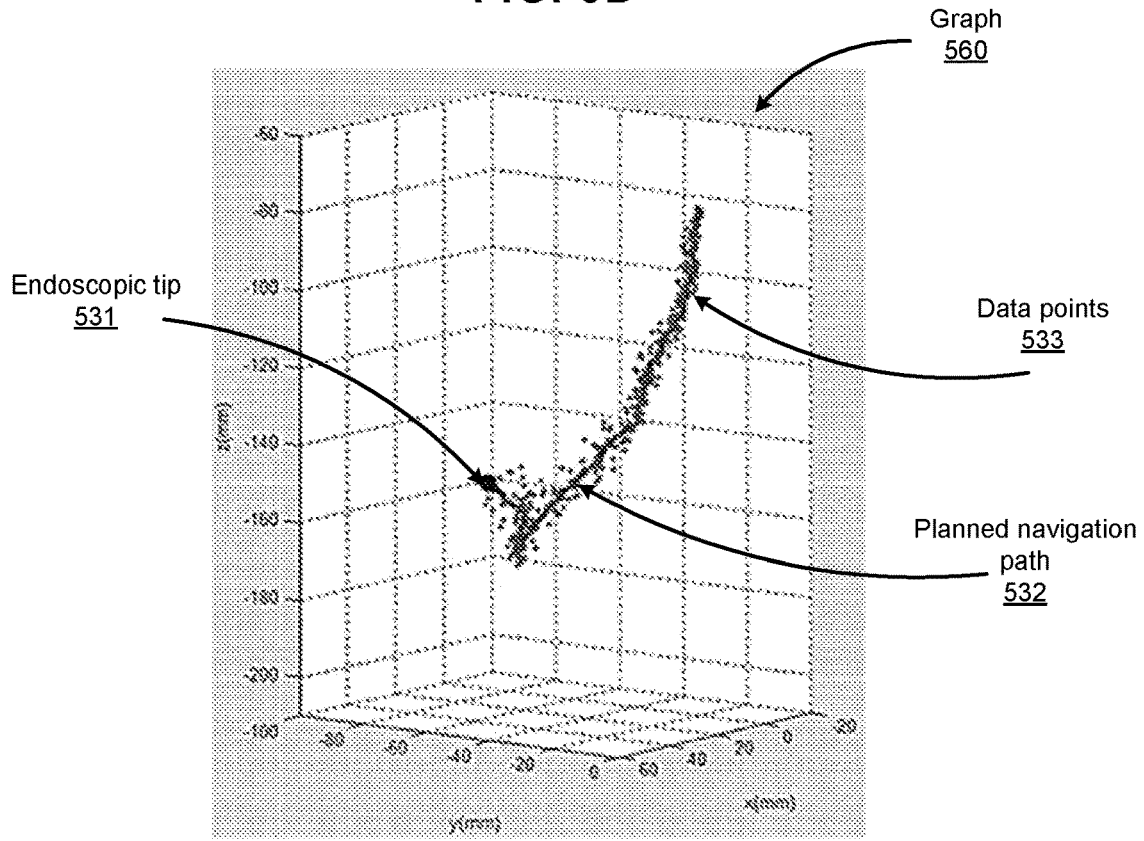

FIG. 5E shows an example graph 560 in which the registered endoscope tip 531 has reached the end of the planned navigation path 532, arriving at the target location in the tubular network, according to one embodiment. As introduced above in FIGS. 5B-5D, the position of the tip 531 shown in FIG. 5E is an expected location derived from the 3D model rather than an actual location of the tip. As shown in FIG. 5E, the recorded EM data points 533 is now generally tracks along the planned navigation path 532, which represents the tracking of the endoscope tip throughout the procedure. Each data point reflects a transformed location due to the updated registration of the EM tracking system to the 3D model.

In some embodiments, each of the graphs shown in FIGS. 5B-5E can be shown sequentially on a display visible to a user as the endoscope tip is advanced in the tubular network. In some embodiments, the processor can be configured with instructions from the navigation configuration system such that the model shown on the display remains substantially fixed when the measured data points are registered to the display by shifting of the measured path shown on the display in order to allow the user to maintain a fixed frame of reference and to remain visually oriented on the model and on the planned path shown on the display.

VI. Lower Body Surgery

Figure 6A:
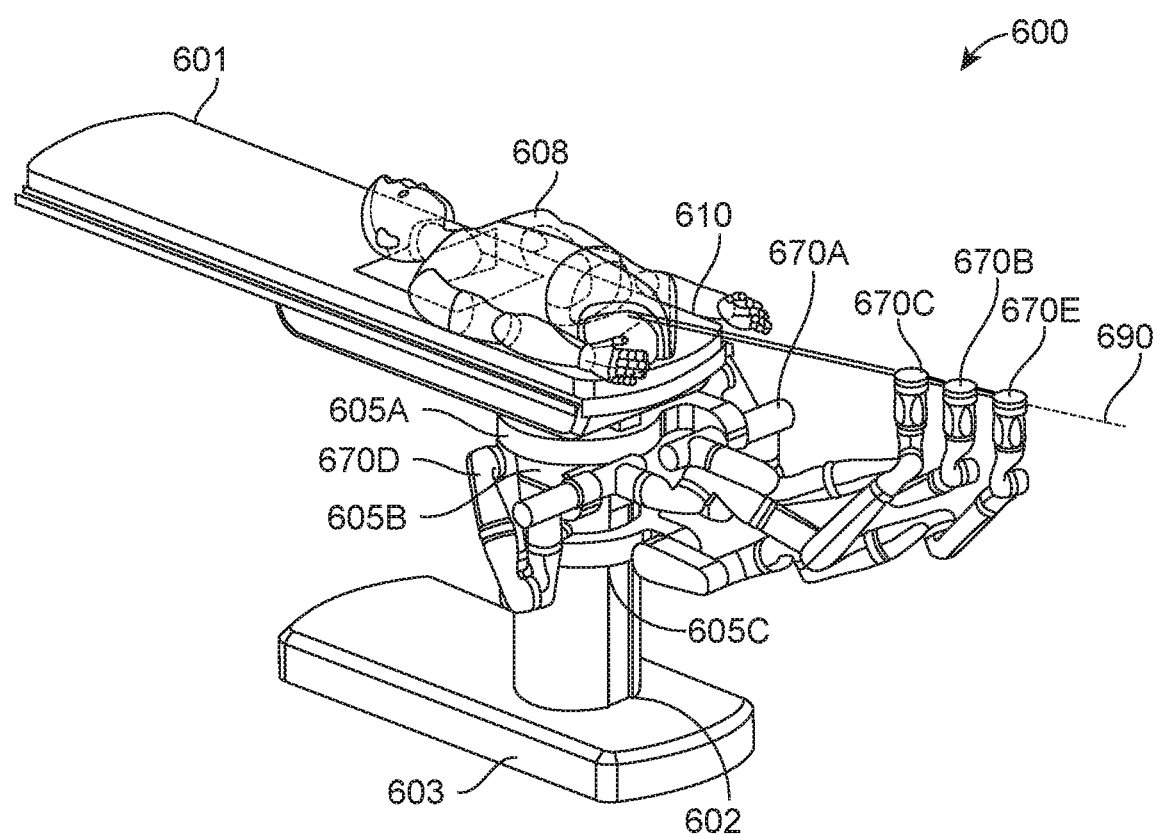
FIG. 6A shows a perspective view of a surgical robotics system with column-mounted arms configured to access the lower body area of a patient according to one embodiment.
Figure 6B:
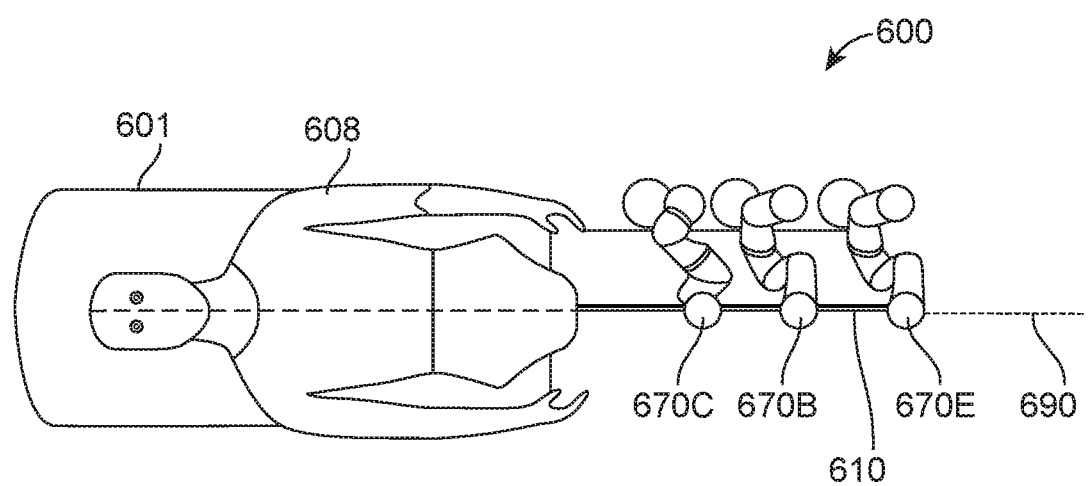
FIG. 6B shows a top view of the surgical robotics system with column-mounted arms configured to access the lower body area of the patient according to one embodiment.

FIGS. 6A-6B show different views of a surgical robotics system with column-mounted arms configured to access the lower body area of a patient according to one embodiment. More specifically, FIG. 6A shows a perspective view of a surgical robotics system 600 with column-mounted arms configured to access the lower body area of a patient 608 according to one embodiment. The surgical robotics system 600 includes a set of robotic arms (including five robotic arms in total) and a set of three column rings. A first robotic arm 670A and a second robotic arm 670B are coupled to a first column ring 605A. A third robotic arm 670C and a fourth robotic arm 670D are coupled to a second column ring 605B. A fifth robotic arm 670E is coupled to a third column ring 605C. FIG. 6A shows a wireframe of the patient 608 lying on the table 601 undergoing a surgical procedure, e.g., ureteroscopy, involving access to the lower body area of the patient 608. Legs of the patient 608 are not shown in order to avoid obscuring portions of the surgical robotics system 600.

The surgical robotics system 600 configures the set of robotic arms to perform a surgical procedure on the lower body area of the patient 608. Specifically, the surgical robotics system 600 configures the set of robotic arms to manipulate a surgical instrument 610. The set of robotic arms insert the surgical instrument 610 along a virtual rail 690 into the groin area of the patient 608. Generally, a virtual rail 690 is a co-axial trajectory along which the set of robotic arms translates a surgical instrument (e.g., a telescoping instrument). The second robotic arm 670B, the third robotic arm 670C, and the fifth robotic arm 670E are coupled, e.g., holding, the surgical instrument 610. The first robotic arm 670A and the fourth robotic arm 670D are stowed to the sides of the surgical robotics system because they are not necessarily required to for the surgical procedure—or at least part of the surgical procedure—shown in FIG. 6A. The robotic arms are configured such that they manipulate the surgical instrument 610 from a distance away from the patient 608. This is advantageous, for example, because there is often limited space available closer toward the patient's body or there is a sterile boundary around the patient 608. Further, there may also be a sterile drape around surgical equipment. During a surgical procedure, only sterile objects are allowed pass the sterile boundary. Thus, the surgical robotics system 600 may still use robotic arms that are positioned outside of the sterile boundary and that are covered with sterilized drapes to perform a surgical procedure.

In one embodiment, the surgical robotics system 600 configures the set of robotic arms to perform an endoscopy surgical procedure on the patient 608. The set of robotic arms hold an endoscope, e.g., the surgical instrument 610. The set of robotic arms insert the endoscope into the patient's body via an opening in the groin area of the patient 608. The endoscope is a flexible, slender, and tubular instrument with optical components such as a camera and optical cable. The optical components collect data representing images of portions inside the patient's body. A user of the surgical robotics system 600 uses the data to assist with performing the endoscopy.

FIG. 6B is a top view of the surgical robotics system 600 with column-mounted arms configured to access the lower body area of the patient 608 according to one embodiment.

VII. Basket Apparatus

Figure 7A:
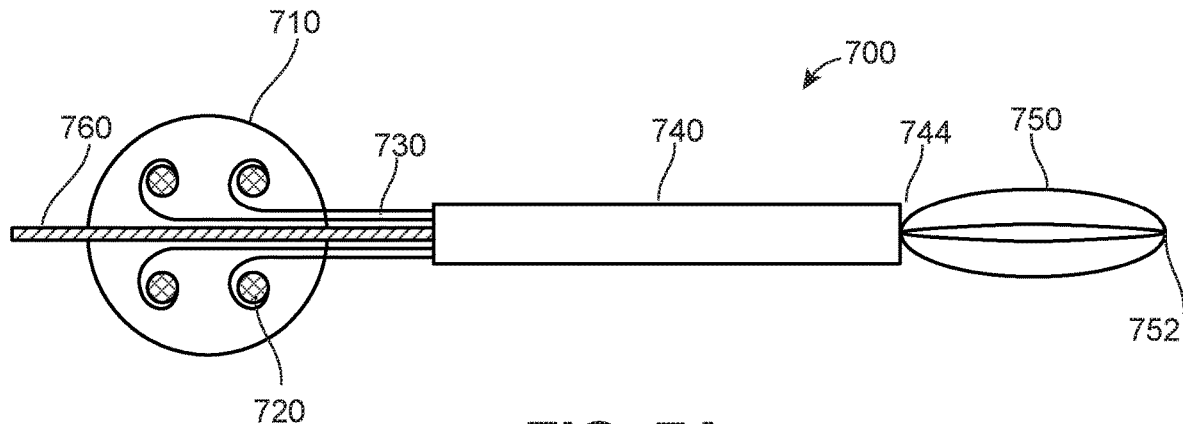
FIG. 7A shows a side view of a basket apparatus of a surgical robotic system, according to one embodiment.
Figure 7B:
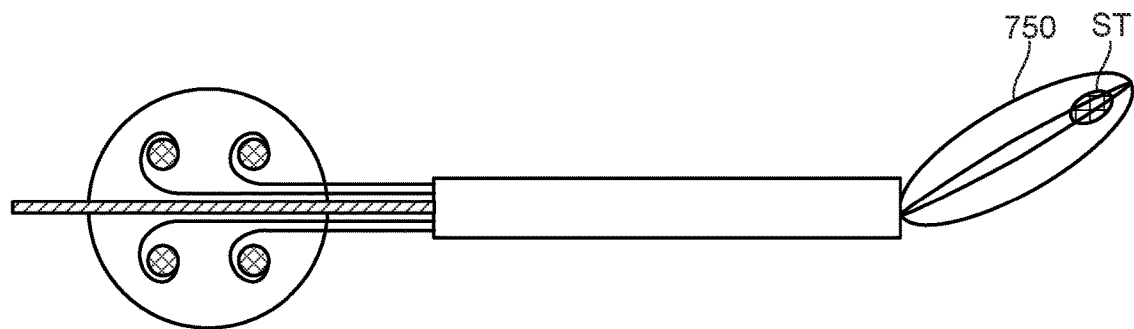
FIGS. 7B and 7C show how the basket apparatus may be used to capture a kidney stone, according to one embodiment.
Figure 7C:
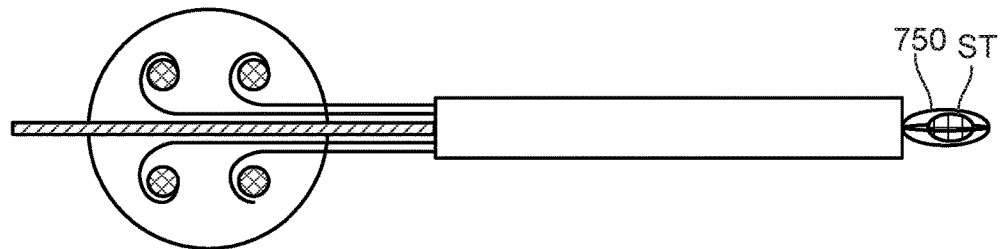

FIGS. 7A-7B show a side view of a basket apparatus 700 of a surgical robotic system and how the basket may be used to capture a kidney stone, according to one embodiment. More specifically, FIG. 7A shows a side view of the basket apparatus 700, according to one embodiment. FIGS. 7B and 7C show how the basket apparatus 700 may be used to capture an object, such as a urinary stone, according to one embodiment.

The robotically steerable basket apparatus 700 may be operatively and removably coupled to any of the IDMs described herein and above, such as IDM 117 described above. The robotically steerable basket apparatus 700 may be advanced through a natural or artificially created orifice in a subject or patient to capture a target object within the body of the subject or patient. For instance, the robotically steerable basket apparatus 700 may be advanced with the surgical robotic system 100 through the urethra, and optionally the bladder, ureter, and/or the kidney to capture a kidney stone (ST). As another example, the robotically steerable basket apparatus 700 may be advanced into the gallbladder to capture a gallstone. In some embodiments, the robotically steerable basket apparatus 700 may be advanced through another working channel of a catheter, ureteroscope, endoscope, or similar device (e.g., within a 1.2 mm diameter working channel.)

The robotically steerable basket apparatus 700 may include a handle or tool base 760 adapted to removably and operatively couple with the IDM 117. The tool base 760 may include a number of capstans 720 to couple to the output shafts or drive units of the IDM so that the IDM can actuate the capstans 720 as well as other actuation elements coupled thereto. The basket apparatus 700 further includes a number of pull wires (also referred to as tendons) 730. The pull wires 730 are coupled to the capstans 720 at one end. The pull wires 730 run straight along the long axis of the apparatus 700, and are prevented from sagging or twisting by an elongate support shaft 740. The elongate support shaft 740 includes a plurality of lumens and channels through which the pull wires 730 may traverse along the direction of the long axis of the apparatus 700. The elongate support shaft 740 may be flexible to facilitate advancement of the basket apparatus 700 through a tortuous tissue tract or bodily channel, such as the urethra and ureter.

The pull wires 730 may be coupled to one another at the distal-most tip 752 of the basket apparatus 700. For example, the basket apparatus 700 may include two different pairs of pull wires 730, with each pull wire pair forming a loop with the tips of the loops coupled to one another at tip 752 and each pull wire having its two ends threaded through opposite peripheral channels or lumens of the elongate support shaft 740. The two tips of the looped pull wires may be coupled together in any number of ways. For example, they may be soldered together, crimped together, braided together, bonded together with an adhesive, tied together with a suture or other thread, etc. Once connected together, each pair of pull wires forming a loop can also be referred to as a single pull wire, if that terminology is preferred in a particular implementation.

When the tool base 760 is coupled to an IDM, the capstans 720 may actuate the pull wires 730 so that the pull wires 730 can be translated proximally or distally in the axial (long axis) direction, such as relative to the elongate support shaft 740. One or more of the pull wire 730 may be translated independently from one another, such as by their respective capstans 720.

The distal ends of the pull wires 730 may extend from the distal end 744 of the elongate support shaft 740 to form a distal wire basket 750. The distal ends of the pull wires 730 may be retracted by the capstans 720 located at the proximal end of the elongate support shaft 740 to collapse the basket 750 into the elongate support shaft 740. Retraction of the basket 750 into the elongate support shaft 740 can lower the profile of the basket apparatus 700 to facilitate the advancement of the basket apparatus 700 into a tissue tract or bodily channel. Conversely, the capstans 720 may be actuated to extend the pull wires 730 out from the elongate support shaft 740 so that the basket 750 may expand. For instance, once the distal end 744 of the elongate support shaft 740 is positioned near a stone ST, the basket 750 may be expanded to capture the stone ST.

The basket 750 may be extended from elongate support shaft 740 at different amounts of extension to vary the size of the basket 750. For instance, as illustrated in FIGS. 7B and 7C, the basket 750 may initially be extended to an enlarged size to capture the stone ST within the basket 750 and then the basket 750 may be partially collapsed (i.e., reduced in size) to secure the stone within the basket 750. As further shown in FIG. 7B, the pull wires 730 may be selectively actuated to steer or tip the basket 550 to facilitate capture of the stone ST. The elongate support shaft 540 may be held stationary relative to the pull wires 530 while the pull wires 530 are differentially actuated. The basket 750 may be steered in any number of directions by the differential actuation of the individual pull wires 730 such that it has a 360° range of motion. For example, one end of an individual pull wire 730 may be held stationary while the other end is pulled or pushed to tip the basket 750 toward or away from the moving end, respectively. In other examples, the individual ends of the pull wires 730 may be differentially pulled, pushed, or held stationary to vary the degree and/or direction of the tipping.

The degree of movement of the capstans 720 may be indicative of the degree and/or direction of the tipping of the basket 750 and also of its current size. Therefore, in some embodiments, the robotic system, and the IDM in particular, can determine and/or track the current configuration of the basket 750 positioned within a subject or patient's body based on the feedback or information from the capstans 720, the drive unit(s), or output shaft(s) and without visualization of the basket 750. Alternatively or in combination, the basket 750 may be visualized to determine and/or track its current configuration. The pull wires 730 may be formed from a shape memory material or metal (e.g., a Nickel-Titanium alloy such as Nitinol) so that the distal ends of the pull wires 730 may be biased to assume the basket shape when unconstrained and/or at body temperature.

VIII. Object Sizing System

Figure 8:
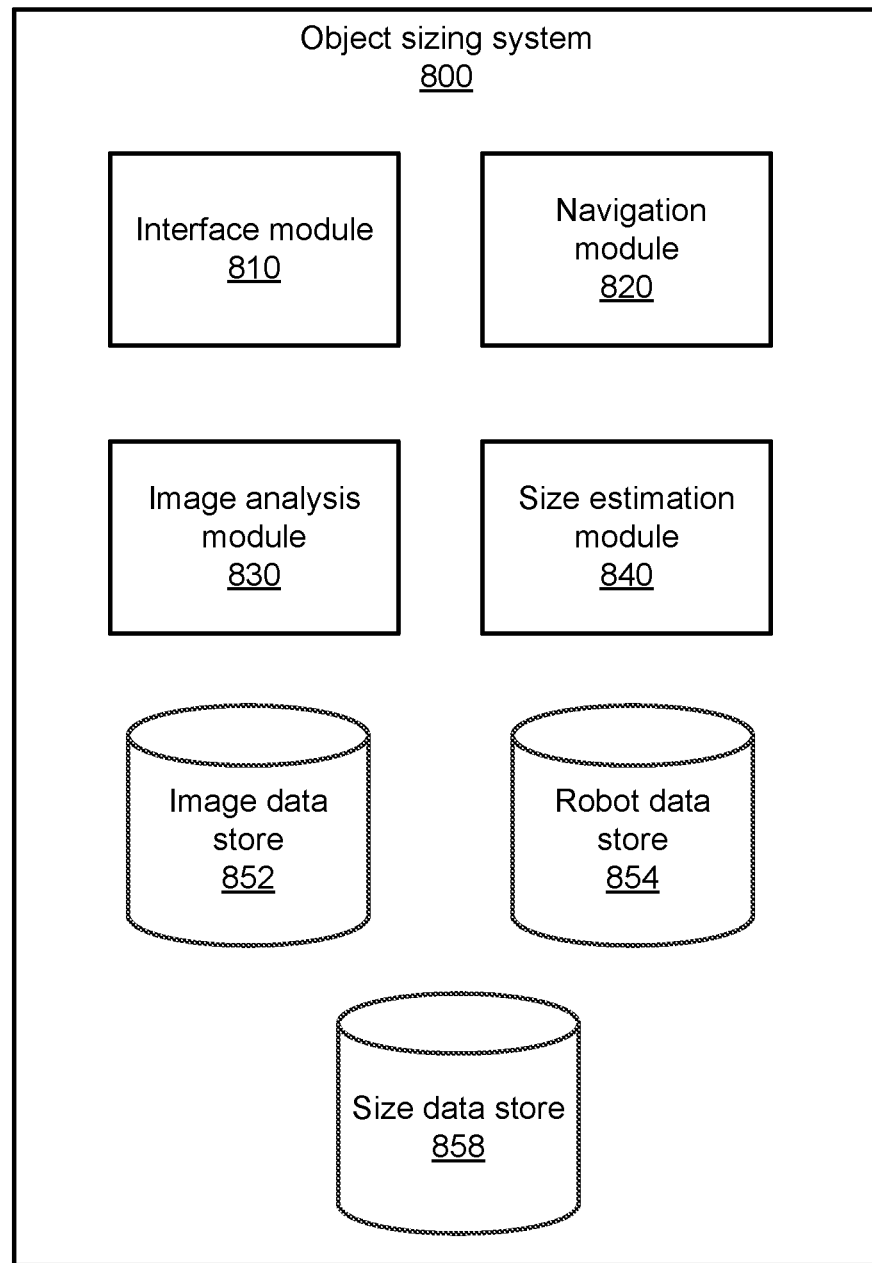
FIG. 8 shows an example block diagram of an object sizing system, according to one embodiment.

FIG. 8 shows an example block diagram of an object sizing system 800, according to one embodiment. In FIG. 8, the object sizing system 800 includes multiple data stores including input data stores such as an image data store 852, a robot data store 854, and an output data store, a size data store 858. The object sizing system 800 also includes multiple modules.

The interface module 810 receives various of input data from input devices (EM sensor, imaging sensor, IDMs) of the surgical robotic system 100. The interface module 810 may also provide the output data (e.g., estimated size of the target object) to a user.

The navigation module 820 navigates the endoscopic tool through the tubular network of the patient's body to arrive at an anatomical site within a lumen of the tubular network, for example, near the position where the target object locates. The navigation module 820 also instructs the endoscopic tip to be positioned with a particular orientation proximal to the target object. A sequence of images of the object are captured by the imaging sensor while the endoscopic tip is positioned in a particular location with a specific orientation proximal to the target object. The navigation module 820 navigates the endoscopic tool to arrive at different positions with different orientations proximal to the target object, and images of the object are captured while the endoscopic tool is at each of those positions and orientations.

The image analysis module 830 analyzes the images of the object captured by the imaging sensor when the endoscopic tool is located at different positions with specific orientations proximal to the target object. In more detail, the image analysis module 830 extracts various input data (e.g., image data, robot data, EM data) stored in the input data stores 852-856 and employs various image analysis techniques (e.g., image stitching techniques, optical flow techniques) for estimating a size of the target object, as more fully described below with reference to FIGS. 10-13.

The size estimation module 840 determines an estimated size of the target object based on the analysis performed by the image analysis module 830, and stores the size data in the size data store 858.

The block diagram of the object sizing system 800 shown in FIG. 8 is merely one example, and in alternative embodiments not shown, the object sizing system 800 can include different and/or addition entities. Likewise, functions performed by various entities of the system 800 may differ according to different embodiments.

The input data, as used herein, refers to raw data gathered from and/or processed by input devices (e.g., command module, imaging sensor, EM sensor, IDM) for generating an estimated size of the target object. Each type of the input data stores 852-856 stores the name-indicated type of data for access and use by the multiple modules 810-840.

Image data may include one or more image frames captured by the imaging sensor at the instrument tip, as well as information such as sequence of the captured images, frame rates or timestamps that allow a determination of the time elapsed between pairs of frames. The size data store 858 receives and stores size data provided by the size estimation module 840. The size data describes an estimated size of the target object. Example size data includes size data like absolute outer axial diameter of the object. Example size data also includes size data describing size of the object in relation to environment surrounding the object, e.g., size of the object compared with diameter of lumen (e.g., ureter) and/or basket capturing the object. The estimated size may, for example, also indicate whether or not the object fits in the basket. The estimated size of the object may also be described in relation to shape of the object. For example, for a round object like a stone, the estimated size of the object indicates outer axial diameter of the object from all directions.

Robot data includes data related to physical movement of the endoscopic tool or part of the endoscopic tool (e.g., the endoscopic tip or sheath) within the lumen. Example robot data includes both command data and actual motion data. The command data describes commands by the surgical robotic system for instructing the endoscopic tip to reach a specific anatomical site and/or change its orientation (e.g., motion of one or more pull wires, tendons or shafts of the endoscope), and can be provided by the IDMs. The actual motion data describes actual motion of the endoscopic tip, and can be provided by EM sensors or deduced from other data such as image data collected from the imaging sensor at the distal tip of the endoscope (the endoscopic tip).

For the purposes of the techniques described herein, in one embodiment, the actual motion data provides the same information about positions and movements of the endoscopic tip as provided by the command data describing the commands that instructs the tip to reach these positions and to achieve these movements. In another embodiment, the actual motion data provides different information about positions and movements of the tip from the corresponding command data, as the endoscopic tip may not strictly follow corresponding commands. In this case, actual motion data may be used to calibrate command data and/or otherwise provide supplemental data that helps verify the motion of the endoscopic tip.

Regardless of whether command data or actual motion data in practice, both types of data are capable of providing information that describes insertion, position, and articulation of the endoscopic tool during the course of a procedure. As one example, the information provided can include insertion information indicating the depth the endoscopic tool as a whole inside a lumen or inside a patient's body, position information indicating the position of the endoscopic tip relative to the object, and articulation information indicating orientation (e.g., pitch, raw, and yaw) of the endoscopic tip in relation to the object.

The object sizing system 800 may further use any information it generates to further provide information to an operator and/or generate recommendations based on that information to provide to an operator. This may include, for example, information about whether the basket can fit the object based on their relative sizes, whether the object will fit down the working channel of the instrument or through a percutaneous port in a patient, whether the object should be broken before removal, etc.

VIII. A. General Object Sizing Process

Figure 9:
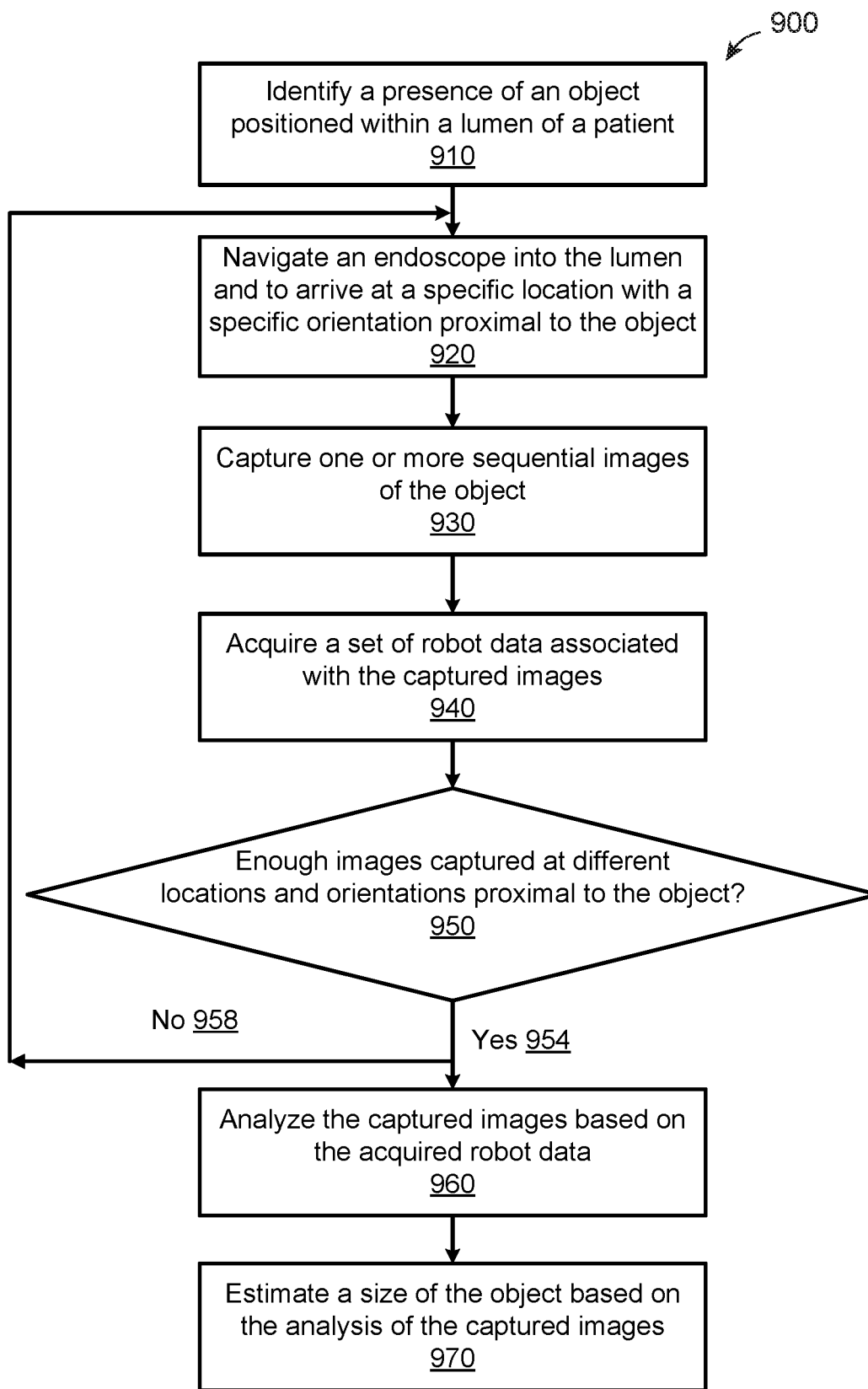
FIG. 9 shows an example flowchart illustrating a process of estimating size of an object within a lumen of a patient's body by the object sizing system shown in FIG. 8, according to one embodiment.

FIG. 9 shows an example flowchart 900 illustrating a process of estimating size of an object within a lumen of a patient's body by the object sizing system shown in FIG. 8, according to one embodiment. As shown in FIG. 9, initially, the object sizing system 800 identifies 910a presence of an object (e.g., a kidney stone) positioned within a lumen of a patient. Upon identification of the object, the object sizing system 800 navigates 920 an endoscope into the lumen to arrive at a specific location with a specific orientation proximal to the object. The object sizing system 800 instructs the imaging sensor to capture 930 one or more sequential images of the object at the specific location with the specific orientation. The object sizing system 800 also acquires 940 a set of robot data associated with the captured images. Specifically, for each of the captured images, there is robot data describing the endoscope motion as well as position measurements of the endoscope and the object for that image.

If the captured images are inadequate 958 to determine the object size, the object sizing system 800 navigates 920 the endoscope to a different location with a specific orientation proximal to the object, and instructs the imaging sensor to capture 930 one or more additional sequential images of the object at that location with the specific orientation. As described below, the object sizing system 800 is capable of estimating a size of the object with improved accuracy with images captured at different positions with same or different orientations proximal to the object, compared with using images at only a single location.

After sufficient images of the object are captured 954 with the endoscope at multiple locations and/or orientations in relation to the object, the object sizing system 800 analyzes 960 the captured images based on the acquired robot data. The object sizing system 800 estimates 970 a size of the object based on the analysis of the captured images.

VIII. B. Object Size Estimation Techniques Using Image Analysis

VIII. B. 1 Image Stitching Techniques

Figure 10:
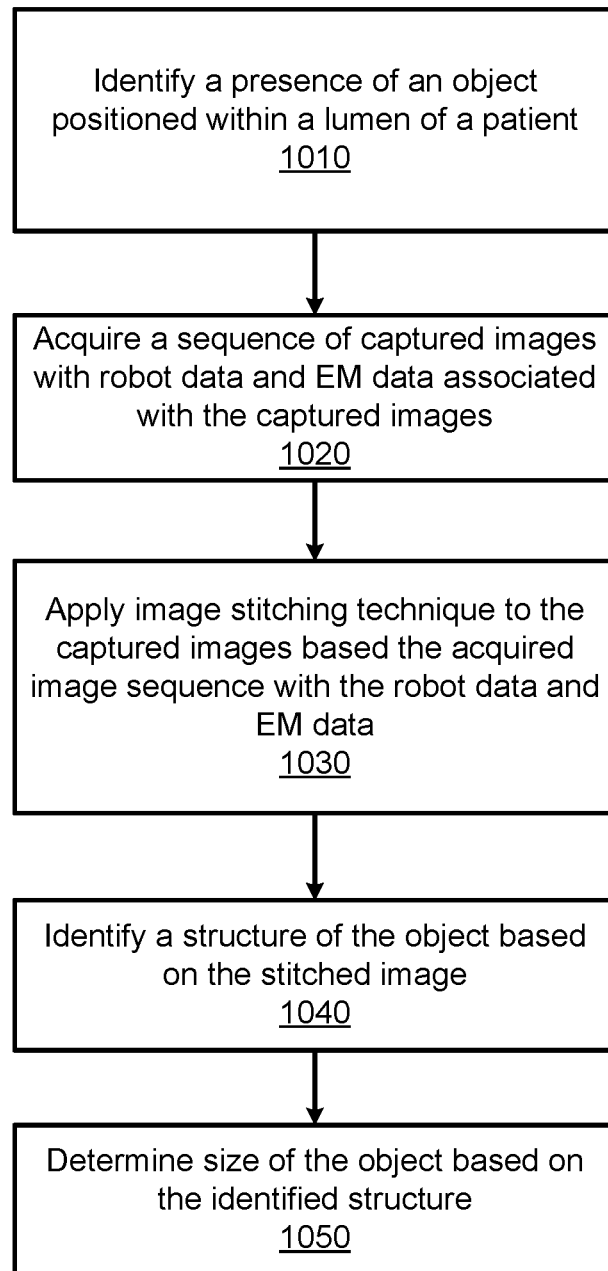
FIG. 10 shows an example flowchart illustrating a process of estimating size of the object using image stitching techniques, according to one embodiment.

FIG. 10 shows an example flowchart illustrating a process of estimating size of an object using image stitching techniques, according to one embodiment. As introduced above, the object sizing system 800 identifies 1010 a presence of an object positioned within a lumen of a patient.

The object sizing system 800 also acquires 1020 a sequence of captured images with robot data and EM data associated with the captured images. In one embodiment, the images are captured with the endoscope (specifically an imaging sensor coupled to the endoscopic tip) moved to be positioned at different locations in relation to the object. As one example, the object sizing system 800 instructs the endoscope to move to different depths in the lumen where the object locates, as represented by insertion data. As another example, at a fixed or varied depth into the lumen, the object sizing system 800 instructs the imaging sensor of the endoscope to be positioned at different locations (e.g., left, right) relative to the object, as represented by position measurements. As a further example, at a fixed or varied depth in the lumen and at a fixed or varied location relative to the object, the object sizing system 800 instructs the imaging sensor to articulate around the object, and as represented articulation data. The robot data acquired such as the insertion data, position measurements, and articulation data describes these various motion of the endoscope and the imaging sensor accordingly in relation to the object, which allows the object sizing system 800 to derive a complete understanding of the various motions of the imaging sensor and thereby deduce an accurate estimate of the object size.

The object sizing system applies 1030 image stitching techniques to the captured images based on the acquired image sequence along with the robot and/or EM data received for the periods of time when the image sequence was acquired. The object sizing system 800 is capable of stitching multiple captured images together to create a 3D model of the object. As one example for stitching two images (e.g., Image A and Image B) together, the object sizing system 800 acquires EM and/or robot data associated with the captured images. This data indicates positions of the object shown in these two images, for example, spatial measurements of the object like x, y, z (Cartesian) coordinates, as well as orientation (angular coordinates) of the camera while the camera is capturing those images. More details about the EM data and robot data that can provide these coordinates can be found in patent application Ser. No. 15/268,238 that is hereby incorporated by reference in its entirety. The object sizing system 800 identifies overlapped portion between Image A and Image B based on the EM data and/or robot data, and stitches these two images together to create a combined image based on the identified overlapped portion. To create a 3D model of the object, the object sizing system 800 may stitch multiple images taken from different views of the object. Example stitching algorithms include 3D stitching, normalized stitching, least squares matching, normalized cross correlation and stitching algorithms based on normalized mutual information.

The object sizing system identifies 1040 the structure based on the created 3D model. The structure may include a shape and a size of the object. The identified structure can be a 3D shape of the object, and example metrics of the 3D shape include longest axis and/or shortest axis of the object and other metrics. For example, the identified structure may include an approximate radius or outer axial diameter or radius of a round kidney stone. The object sizing system 800 determines 1050 an estimated size of the object based on the identified structure.

VIII. B.2 Basketing Techniques
VIII. B. 2.1 Basket Marker Detection

Figure 11A:
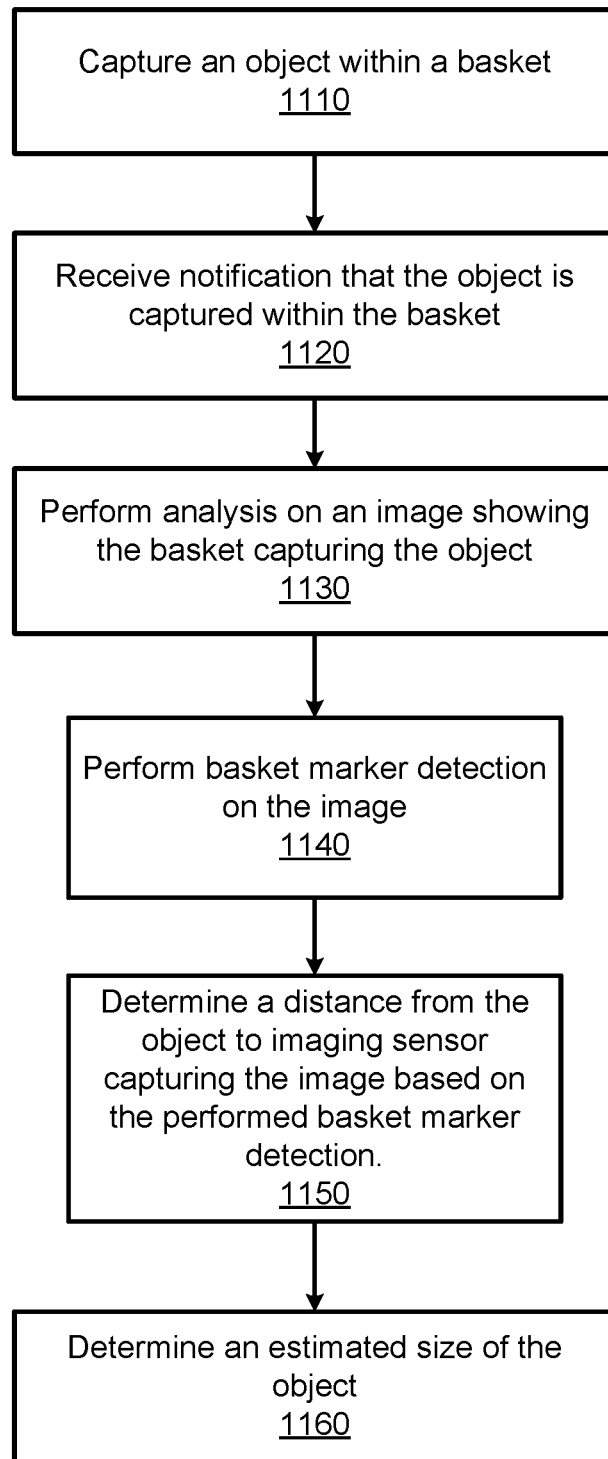
FIG. 11A shows an example flowchart illustrating a process of estimating size of an object using basket marker detection, according to one embodiment.

FIG. 11A shows an example flowchart illustrating a process of estimating size of an object using a basketing apparatus and basket marker detection, according to one embodiment. The object sizing system 800 instructs a basket apparatus to capture 1110 an object within a basket. For example, the basket apparatus can be the basket apparatus 700 shown in FIGS. 7A-7C, and the object is an object (e.g., a kidney stone) within a lumen of a patient's body.

After receiving 1120 notification that the object is captured within the basket, the object sizing system 800 performs 1130 analysis on an image showing the basket capturing the object. The analyzed image can be a singular image captured by the imaging sensor or a stitched image created by stitching together multiple images as introduced in the prior section.

The image analysis performed by the object sizing system 800 includes performing basket marker detection 1140 on the image. In this case, the basketing apparatus is assumed to include visually distinctive markers offset at fixed intervals from each other on the wires of the basket. The object sizing system 800 determines 1150 a distance from the object to the imaging sensor of the endoscope capturing the image based on the locations of the markers within the image.

In a variation on this technique, in addition to or in place of markers on the basketing apparatus, a guide wire may be inserted into the patient and placed in front of the imaging sensor of the endoscope or basketing apparatus, for example through the working channel of either of those instruments. The guide wire may similarly include visually distinctive markers. Based on known or tabulated information on the insertion depth of the guide wire and/or based on any markers present on the guide wire, the distance between the object and the imaging sensor of the endoscope can also be determined.

VIII. B.2. II. Known Motion from a Robotically Controlled Basket

Figure 11B:
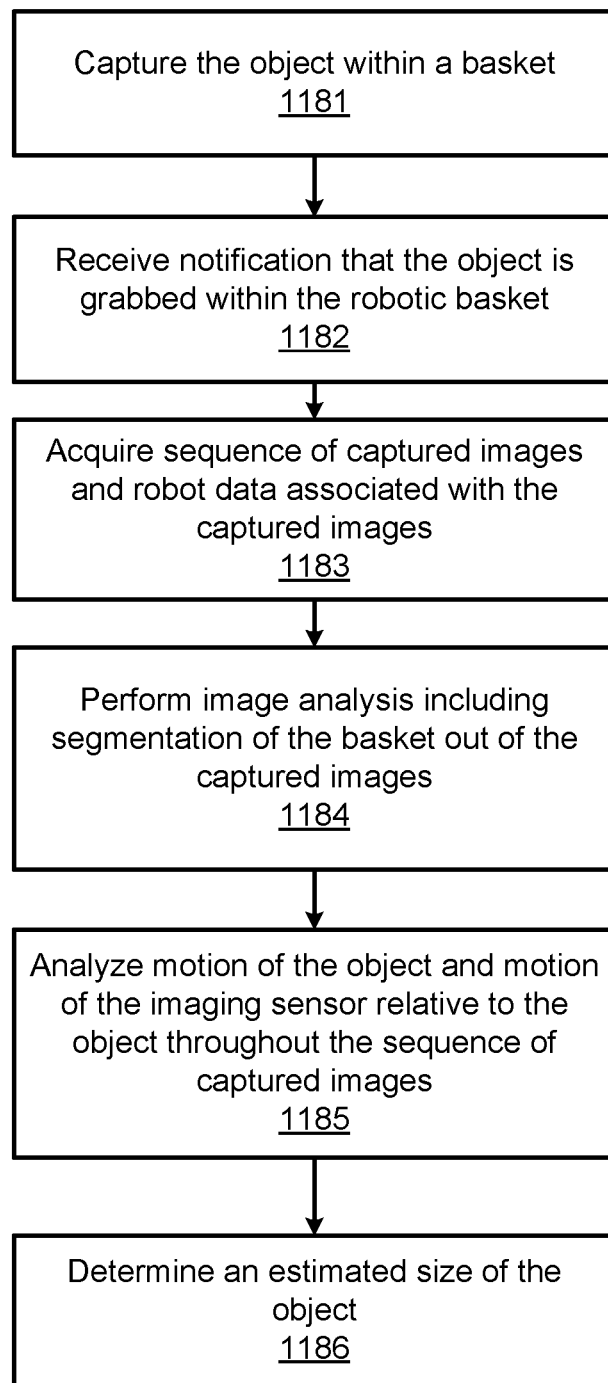
FIG. 11B shows an example flowchart illustrating a process of estimating size of an object using motion detection with a basket capturing the object, according to one embodiment.

FIG. 11B shows an example flowchart illustrating a process of estimating size of an object using motion detection with a basket capturing the object, according to one embodiment. As with the previous section, the object sizing system 800 instructs a basket apparatus to capture 1181 an object within a basket. In this embodiment, the basket apparatus is a robotically controlled basket receiving command instructions from the object sizing system 800 for different movements (e.g., insertion, rotation, etc.) to capture the object. In one embodiment, after receiving 1182 notification that the object is captured within the basket, the object sizing system 800 captures 1183 a sequence of images of the object and also receives robot data associated with the captured images. In the same or a different embodiment, the object sizing system 800 captures 1183 a sequences of images of the object and also receives robot data associated with the captured images, regardless of whether the object is captured in the basket. Generally, however, these images will include at least some set of images containing at least a portion of the basket and at least a portion of the object. To acquire a sequence of images of the object, the object sizing system 800 can instruct the camera to move around the object to take images of the object. The object sizing system 800 can also instruct the camera to stay fixed in position while taking images of the object, which can be easier if the object is moving (e.g., moving according to changes of the endolumenal environment surrounding the object).

The object sizing system 800 performs 1184 image analysis to identify the object. This may include segmenting the images to remove the basket from the images, leaving the object and any other data of interest. Alternatively, the images may be segmented to isolate the basket and object so that they may be analyzed relative to each other. As the basket may be moving between captured image frames, the robot and/or EM data indicates real-time position and movement of the robotically controlled basket, for example, distance of the basket from the camera, which can then be used to determine the size of the basket in the image frames. This information can then be used to identify which portions of the image are due to the basket, which can then be segmented out from the images. The robot and/or EM data also indicates the real-time size of the basket, which can further provide additional useful information, such as an upper bound on the size of the object, which can, for example, be a starting point in a more rigorous calculation of the size of the object.

The object sizing system 800 analyzes 1185 motion of the object and motion of the imaging sensor as provided by the robot data throughout the sequence of the captured images. As described above, the robot data describes endoscope motion such as insertion, articulation as well as position measurements of the object and the endoscope's imaging sensor. Thus, the robot data allows the object sizing system 800 to derive the motion of the imaging sensor. Once the motion of the imaging sensor is determined, this can subtracted out to isolate the motion of the object by removing motion associated with the imaging sensor.

Once the motion of the object has been isolated, the object sizing system 800 can further analyze the motion of the object to identify its structure. As above, structure may include shape and estimated size. For example, if the object is rotating throughout the sequence of images, that rotation may provide a more complete 3D picture of the object's shape that otherwise may not be able to be obtained due to limitations in the repositionability of the imaging sensor. Specifically, the object sizing system 800 determines 1186 an estimated size of the object. As described above in step 1884, the object sizing system 800 can use pixels of the remaining portions of the captured images after segmenting out the basket to determine an estimated size of the object.

VIII. B. 3 Illumination Pattern Analysis

Figure 12:
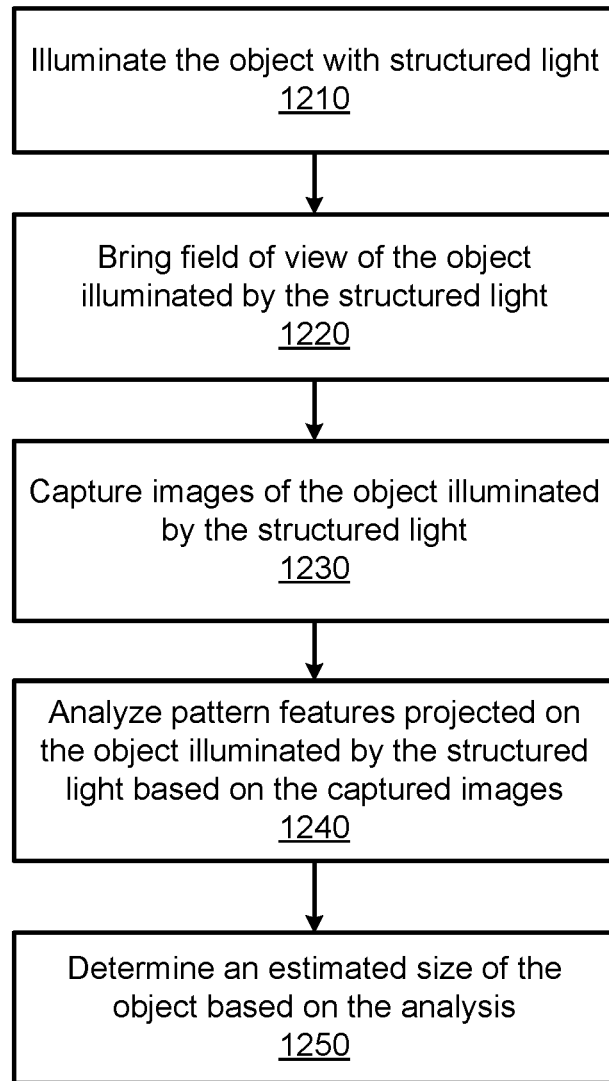
FIG. 12 shows an example flowchart illustrating a process of estimating size of an object illuminated by structured light within a lumen of a patient's body, according to one embodiment.

FIG. 12 shows an example flowchart illustrating a process of estimating size of an object illuminated by structured light within a lumen of a patient's body, according to one embodiment. The object sizing system 800 instructs the illumination source of the endoscope to illuminate 1210 the object with structured light. The structured light may contain a pattern that is projected on the object. The object sizing system 800 is navigated 1120 so that the field of view of the endoscope's imaging sensor includes the object and the pattern of structured light projected thereupon. The object sizing system 800 then instructs the imaging sensor to capture 1230 images of the object. The object sizing system 800 analyzes 1240 how the reflection of the pattern is modified by being projected on and reflected by the object. Generally objects will have non-planar structure along a plane perpendicular to the imaging sensor central axis, and so the reflection of the pattern will appear differently versus what is projected from the illumination source. The reflection of the structured light may also vary depending on materials of the object. As one example, objects that have different materials such as plastic or metal can have different reflection patterns based on same structured light. As another example, objects that are composed of different proportions of the same materials (e.g., stones made up of different calcium concentrations) can also have different reflection patterns based on the same structured light. The object sizing system 800 can analyze pattern features projected on the object based on a single image. The object sizing system 800 can also analyze pattern features by combining multiple images captured from different views to create a complete 3D model based on robot data describing the different views. Changes in the pattern structure can be mathematically computed to determine the structure of the object. The object sizing system 800 can then determine 1250 an estimated size or other aspects of the structure of the object based on the analysis.

VIII. B. 4 Motion Detection with Robot Data or Optical Flow

Figure 13:
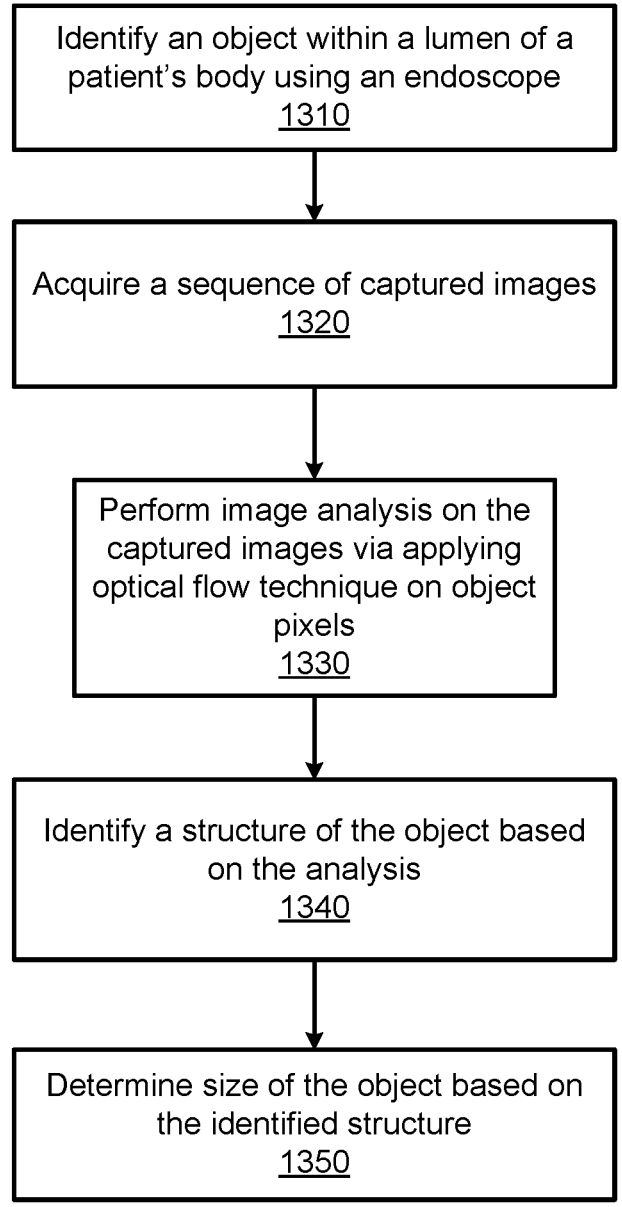
FIG. 13 shows an example flowchart illustrating a process of estimating size of an object within a lumen of a patient's body employing motion detection using robot data or optical flow techniques, according to one embodiment.

FIG. 13 shows an example flowchart illustrating a process of estimating size of an object within a lumen of a patient's body employing motion detection using robot data or optical flow techniques, according to one embodiment. The object sizing system identifies 1310 an object within a lumen of a patient's body using an endoscope. The object sizing system 800 acquires 1320 a sequence of captured images of the object. The object sizing system 800 performs 1330 image analysis on the captured images by applying optical flow technique on object pixels. In more detail, the object sizing system 800 isolates the identified object shown in the captured images from the rest of the images, and applies optical flow technique only to the isolated object shown in the images. The pixels relating to identified object shown in the captured images may have particular movement or position change that differ distinctively from those relating to the endolumenal environment surrounding the object. As one example, if the identified object is a kidney stone positioned inside the kidney, the pixels of the stone shown in captured images may reflect movement of the stone according to movement of the ureter. Performing optical flow on the specific pixels depicting the object can therefore provide beneficial information (for navigation, analysis or otherwise) beyond that of optical flow performed, for example, on images as a whole.

To isolate the object from the rest of a captured image, as one example, the object sizing system 800 may segment the object as described in subsection VIII. B. 2. II. The object sizing system 800 may also analyze the captured image by detecting the rigid parts of the object.

While applying optical flow technique to perform image analysis, the object sizing system 800 can use the identified object as a reference point combined with the description of the optical flow techniques described in patent application Ser. No. 15/268,238 that is hereby incorporated by reference in its entirety. For example, if optical flow of captured images is used to perform navigation of an instrument, the optical flow analysis may be augmented by including optical flow analysis of, specifically, the portions of the image depicting the object to provide further information about the movement of the instrument in the patient lumen.

Regardless of the approach used above, the object sizing system 800 analyzes 1340 the motion of the object and imaging sensor relative to the object throughout the sequence of the captured images. The object sizing system 800 identifies 1350 a structure of the object based on the analysis. The object sizing system 800 determines 1360 an estimated size of the object based on the identified structure.

IX. Machine Configuration for the Surgical Robotic System

More generally, the object sizing system techniques disclosed herein may be implemented and performed in conjunction with an appropriately configured computer system. A processor within the computer system may comprise one or more components to process electronic signals, and may comprise one or more of a central processor unit, a video processor, logic circuitry, gate array logic, filed programmable gate array, integrated circuit, or application specific integrated circuit. The computer system includes a central processing unit (CPU, also "processor" and "computer processor" herein), which can be a single core or multi core processor, or a plurality of processors for parallel processing. The CPU can execute a sequence of machine-readable instructions, which can be embodied in a program or software. The instructions may be stored in a memory location. Examples of operations performed by the CPU can include fetch, decode, execute, and writeback. The CPU can be part of a circuit, such as an integrated circuit. One or more other components of the system can be included in the circuit. In some cases, the circuit comprises an application specific integrated circuit (ASIC).

The computer system may also include one or more of memory or memory locations (e.g., random-access memory, read-only memory, flash memory), electronic storage units (e.g., hard disk), communication interfaces (e.g., network adapters) for communicating with one or more other systems, and peripheral devices, such as caches, other memory, data storage and/or electronic display adapters. The memory, storage unit, interface, and peripheral devices are in communication with the CPU through a communication bus, such as a motherboard.

The storage unit can be a data storage unit (or data repository) for storing data. The computer system can be operatively coupled to a computer network ("network") with the aid of the communication interface. The network can be the Internet, an internet and/or extranet, or an intranet and/or extranet that is in communication with the Internet. The network in some cases is a telecommunication and/or data network, and can include can include one or more computer servers. The storage unit can store files, such as drivers, libraries and saved programs. The storage unit can store user data, e.g., user preferences and user programs. The computer system in some cases can include one or more additional data storage units that are external to the computer system, such as located on a remote server that is in communication with the computer system through an intranet or the Internet.

Methods as described herein can be implemented by way of machine (e.g., computer processor) executable code stored on an electronic storage location of the computer system, such as, for example, on the memory or electronic storage unit. The machine executable or machine readable code can be provided in the form of software. During use, the code can be executed by the processor. In some cases, the code can be retrieved from the storage unit and stored on the memory for ready access by the processor. In some situations, the electronic storage unit can be precluded, and machine-executable instructions are stored on memory.

The code can be pre-compiled and configured for use with a machine have a processor adapted to execute the code, or can be compiled during runtime. The code can be supplied in a programming language that can be selected to enable the code to execute in a pre-compiled or as-compiled fashion.

Methods and systems of the present disclosure can be implemented by way of one or more methods. A method can be implemented with a processor as described herein, for example by way of software upon execution by one or more computer processors.

X. Additional Considerations

Upon reading this disclosure, those of skill in the art will appreciate still additional alternative structural and functional designs through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context unless otherwise explicitly stated.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present). In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

What is claimed is:

1. A method for analyzing an object positioned within a patient, comprising:
    navigating an elongate body to a location within the patient and proximate to the object;
    capturing sequential images of the object with an imaging sensor;
    navigating the elongate body into different orientations, different positions, or both, during the capture of the sequential images;
    determining orientations and positions of the elongate body during the capture of the sequential images based on a set of sensor data;
    comparing the orientations and positions of the elongate body determined based on the set of sensor data for at least one captured sequential image to the orientation and position determined based on the set of sensor data for at least another captured sequential image; and
    analyzing, with a processor, the sequential images of the object and the comparison of the orientations and positions to estimate a shape of the object.

2. The method of claim 1, wherein the at least one captured sequential image depicts a portion of a basket, and wherein the analyzing the sequential images comprises segmenting the at least one captured sequential image to remove the basket from the at least one captured sequential image.

3. The method of claim 1, wherein the set of sensor data comprises at least one of data collected from a robotic manipulator or data collected from an electromagnetic (EM) sensor coupled to the elongate body.

4. The method of claim 3, wherein the data collected from the robotic manipulator comprises command data used to control the robotic manipulator.

5. The method of claim 3, further comprising:
    activating a set of EM coils with an EM field generator; and
    determining actual motion data of the elongate body based on the data collected from the EM sensor.

6. The method of claim 5, further comprising determining a transformation that aligns a first coordinate in an EM coordinate system and a second coordinate in an 3D model coordinate system.

7. The method of claim 6, wherein the transformation is determined during the navigating the elongate body into the at least one of the different orientation or the different position.

8. The method of claim 1, wherein the analyzing the sequential images comprises:
    combining the sequential images via an image stitching technique to acquire a stitched image; and
    estimating the shape of the object based on the stitched image.

9. The method of claim 8, further comprising generating a 3D model of the object based on the stitched image.

10. The method of claim 8, wherein the shape is described based on at least one of an outer axial diameter or a radius for the estimated shape of the object.

11. The method of claim 8, wherein the shape is described based on at least one of a longest axis or a shortest axis.

12. A system for analyzing an object positioned within a patient, the system comprising:
    an elongate body comprising an imaging sensor located at a distal end of the elongate body; and
    a computer comprising instructions that, when executed by a processor of the computer, cause the computer to:
    navigate the elongate body to a location within the patient and proximate to the object;
    capture sequential images of the object with the imaging sensor while navigating the elongate body into different orientations, different positions, or both;
    determine orientations and positions of the elongate body during the capture of the sequential images based on a set of sensor data;
    compare the orientations and the positions of the elongate body determined based on the set of sensor data for at least one captured sequential image to the orientations and the positions determined based on the set of sensor data for at least another captured sequential image; and
    analyze the sequential images of the object and the comparison of the set of sensor data to estimate a shape of the object.

13. The system of claim 12, wherein the at least one captured sequential image depicts a portion of a basket, and wherein the computer further comprises instructions that, when executed by the processor of the computer, cause the computer to segment the at least one captured sequential image to remove the basket from the at least one captured sequential image.

14. The system of claim 12, wherein the set of sensor data comprises at least one of data collected from a robotic manipulator or data collected from an electromagnetic (EM) sensor coupled to the elongate body.

15. The system of claim 14, wherein the data collected from the robotic manipulator comprises command data used to control the robotic manipulator.

16. The system of claim 14, further comprising:
an EM field generator; and
a set of EM coils located on a tip at the distal end of the elongate body,
wherein the computer further comprises instructions that, when executed by the processor of the computer, cause the computer to:
activate the set of EM coils with the EM field generator; and
determine actual motion data of the elongate body based on the data collected from the EM sensor.

17. The system of claim 16, wherein the computer further comprises instructions that, when executed by the processor of the computer, cause the computer to determine a transformation that aligns a first coordinate in an EM coordinate system and a second coordinate in an 3D model coordinate system.

18. The system of claim 17, wherein the computer further comprises instructions that, when executed by the processor of the computer, cause the computer to:
combine the sequential images via an image stitching technique to acquire a stitched image; and
estimate the shape of the object based on the stitched image.

19. The system of claim 18, wherein the computer further comprises instructions that, when executed by the processor of the computer, cause the computer to generate a 3D model of the object based on the stitched image.

20. The system of claim 18, wherein the computer further comprises instructions that, when executed by the processor of the computer, cause the computer to generate a 3D model of the object based on the stitched image.

* * * * *